US012806436B2

(12) United States Patent
Kim et al.

(10) Patent No.: US 12,806,436 B2
(45) Date of Patent: Nov. 24, 2026

(54) APPARATUS FOR TREATING CANCER WITH HIGH-FREQUENCY HYPERTHERMIA USING ANGLE-ADJUSTABLE PARABOLIC-SHAPED ROTATING HIGH-FREQUENCY RADIATING BODY ELECTRODE

(71) Applicants: Beong Ju Kim, Cheonan-si (KR); Soyul Nathaniel John, Opelika, AL (US)

(72) Inventors: Beong Ju Kim, Cheonan-si (KR); Soyul Nathaniel John, Opelika, AL (US)

(73) Assignees: KYOUNG IN ENGINEERING CO., LTD., Gunpo-si (KR); Beong Ju Kim, Cheonan-si (KR); Nathaniel Soyul John, Opelika, AL (US)

( * ) Notice: Subject to any disclaimer, the term of this patent is extended or adjusted under 35 U.S.C. 154(b) by 125 days.

(21) Appl. No.: 19/010,222

(22) Filed: Jan. 6, 2025

(65) Prior Publication Data

US 2026/0192122 A1 Jul. 9, 2026

(51) Int. Cl.
*A61N 5/01* (2006.01)

(52) U.S. Cl.
CPC .................................... *A61N 5/01* (2013.01)

(58) Field of Classification Search
CPC ...................................................... A61N 5/01
See application file for complete search history.

(56) References Cited

U.S. PATENT DOCUMENTS 5,523,578 A * 6/1996 Herskovic ................ A61N 5/01 378/65
2021/0339037 A1* 11/2021 Sun .......................... A61B 5/01

FOREIGN PATENT DOCUMENTS

KR 101659695 B1 * 9/2016 ............ A61N 5/025
KR 101900700 B1 9/2018
KR 1020170183689 A 7/2019

* cited by examiner

*Primary Examiner* — Kiho Kim
(74) *Attorney, Agent, or Firm* — NKL Law; Jae Youn Kim

(57) ABSTRACT

Proposed is an apparatus for treating cancer with high-frequency hyperthermia using an angle-adjustable parabolic-shaped rotating high-frequency radiating body electrode. The apparatus includes an upper end adjustment high-frequency radiating part fixed to and mounted on an upper side portion of a treatment bed on which a patient is lying, the upper end adjustment high-frequency radiating part being configured to move an upper end dish-shaped radiating part that is configured to output a high-frequency signal at a frequency designated by a corresponding control signal to a designated level. Furthermore, the apparatus includes a lower end adjustment high-frequency radiating part fixed to and mounted on a lower side portion of the treatment bed, the lower end adjustment high-frequency radiating part being configured to move a lower end dish-shaped radiating part that is configured to output a high-frequency signal at a frequency designated by a corresponding control signal to a designated level.

3 Claims, 11 Drawing Sheets

APPARATUS FOR TREATING CANCER WITH HIGH-FREQUENCY HYPERTHERMIA USING ANGLE-ADJUSTABLE PARABOLIC-SHAPED ROTATING HIGH-FREQUENCY RADIATING BODY ELECTRODE

BACKGROUND

Technical Field

The present disclosure relates to an apparatus for treating cancer with high-frequency hyperthermia using an angle-adjustable parabolic-shaped rotating high-frequency radiating body electrode. More particularly, the present disclosure relates to an apparatus for treating cancer with high-frequency hyperthermia using an angle-adjustable parabolic-shaped rotating high-frequency radiating body electrode, the apparatus being configured such that an electrode configured to generate and radiate (irradiate, infuse, inject) a high-frequency signal to an affected area of a human body is formed in a rotator shape and a cross-sectional area of the electrode is formed in an oval shape or a parabolic shape, and the apparatus being configured such that an angle of the generated parabola and a radiating direction of the high-frequency signal are adjusted and the entirety of the electrode is moved in up, down, front, rear, left, and right directions within a predetermined range, thereby being capable of intensively radiating the high-frequency signal to the designated affected area.

Furthermore, the present disclosure relates to an apparatus for treating cancer with high-frequency hyperthermia using an angle-adjustable parabolic-shaped rotating high-frequency radiating body electrode, the apparatus being configured such that a light signal of a red color or a selected color is used so as to visually check a position where a high-frequency signal that is not visible is radiated into the human body, thereby being capable of checking that a high-frequency signal radiation position is accurate, thereby further increasing a treatment effect, and reducing a treatment time.

Description of the Related Art

One of the major causes of shortening the average life span of a human in the modern society is cancer. As a treatment method for cancer, there are surgical removal procedures, drug anticancer treatments, radiation anticancer treatments, and so on, and there are advantages and disadvantages of each treatment method, so it is common to combine treatments.

There is a problem that surgical treatment causes damage to normal tissues when the cancer is significantly advanced. In the same manner, when the cancer is significantly advanced, resistance to cancer drugs is increased, and it is difficult to apply the drug anticancer treatment to patients who are weak and have reduced immunity.

In radiation anticancer treatment, due to the recent development of diagnostic imaging technologies such as CT, MRI, and so on, the treatment effect is increased by accurately irradiating only the cancer tissue. Nevertheless, there are many side effects such as destroying normal tissues surrounding the cancer tissues.

In the high-frequency hyperthermia treatment method, alternating current generated by a frequency signal of 100 Hz or more is radiated (infused, irradiated) directly to a patient's affected area in a contact or non-contact manner, thereby raising the temperature of the affected area so as to necrotize the cancer tissue and to prevent the cancer from expanding and spreading. Compared to the surgical procedure, the drug anticancer treatment, the radiation anticancer treatment, the high-frequency hyperthermia treatment method has relatively low side effects and the patient feels little pain, and the use of the high-frequency hyperthermia treatment method is simple and convenient, so that the use of the high-frequency hyperthermia treatment method is spreading widely recently.

As such, it is known that a current caused by a high-frequency signal flowing to an affected area increases the temperature of the affected area. Particularly, the temperature of the cancer cell increases higher than that of the normal cell.

Meanwhile, it is well known that normal cells begin to die at 47 degrees Celsius, whereas cancer cells, unlike normal cells, are naturally destroyed and necrotized at 42 degrees Celsius. These contents provide a treatment principle of a cancer treatment apparatus using high-frequency hyperthermia.

A conventional technology that partially solves this problem is Korean Patent Application Publication No. 10-2017-0183689 (Dec. 29, 2017) having the title name of "HIGH FREQUENCY HYPERTHERMIA CANCER CARE APPARATUS USING TOPICAL ELECTRODE".

FIG. 1 is a view illustrating a functional configuration of an apparatus for treating cancer with high-frequency hyperthermia according to an embodiment of a conventional technology.

Hereinafter, the conventional technology will be described in detail with reference to the accompanying drawing. In the conventional technology, various shapes of tilt patterns are provided and are optionally used in order to gather a high-frequency signal to single point, the high-frequency signal being output from an upper high-frequency radiating body that is positioned directly above an affected area of a patient and a lower high-frequency radiating body that is positioned directly below the affected area of the patient.

Although the conventional technology has an advantage that the generated high-frequency signal is gathered to the single point, there remains a problem in that the position of the same organ may not be consistent relative to a treatment bed and may vary according to the patient's physical condition, which has yet to be resolved.

In addition, in the conventional technology, when the position of the affected organ varies, it is difficult to concentrate and radiate the high-frequency signal on the corresponding affected area. Therefore, a significant time is required to raise the temperature above 42 degrees Celsius at which cancer cells in the affected area undergo necrosis, and such delay causes pain to the patient during treatment.

Meanwhile, in the conventional technology, since it is difficult not to affect normal cells or organs around the affected area, normal tissues may be necrotized along with the affected area, and problems such as a patient complaining of pain while being treated or being easily exhausted are still not solved.

Therefore, it is necessary to develop a technology that accurately concentrates a high-frequency signal on an affected area, even when a patient's physical condition differs and a position of the affected area varies.

In addition, it is necessary to develop a technology which is convenient to use and which increases preference of the treatment by enabling fine adjustment of a high-frequency signal to focus precisely on an affected area even though the affected area is small, increasing the treatment effect, reducing the treatment time, and preventing the temperature of the normal cells of the patient from increasing.

DOCUMENT OF RELATED ART (Patent Document 1) Korean Patent No. 10-1900700 (Sep. 14, 2018) "HIGH FREQUENCY HYPERTHERMIA CANCER CARE APPARATUS USING ROTATING ELECTRODE"

(Patent Document 2) Korean Patent Application Publication No. 10-2017-0183689 (Dec. 29, 2017) "HIGH FREQUENCY HYPERTHERMIA CANCER CARE APPARATUS USING TOPICAL ELECTRODE"

SUMMARY

Accordingly, the present disclosure has been made keeping in mind the above problems occurring in the related art, and an objective of the present disclosure is to provide an apparatus for treating cancer with high-frequency hyperthermia using an angle-adjustable parabolic-shaped rotating high-frequency radiating body electrode, the apparatus being configured such that a cross-sectional area of the high-frequency radiating body electrode radiating a high-frequency signal to an affected area of a patient is formed in a curved shaped of a parabola so that the generated high-frequency signal is concentrated on a specific position.

In addition, another objective of the present disclosure is to provide an apparatus for treating cancer with high-frequency hyperthermia using an angle-adjustable parabolic-shaped rotating high-frequency radiating body electrode, the apparatus being configured such that the high-frequency radiating body electrode configured to radiate a high-frequency signal to an affected area of a patient is formed in any one shape selected from a parabolic wing shape or a parabolic hemispherical shape so that the treatment effect is increased.

Meanwhile, still another objective of the present disclosure is to provide an apparatus for treating cancer with high-frequency hyperthermia using an angle-adjustable parabolic-shaped rotating high-frequency radiating body electrode, the apparatus being configured such that a position of the high-frequency radiating body electrode configured to radiate a high-frequency signal to an affected area of a patient is moved in up and down directions and front, rear, left, and right directions so that the high-frequency signal is concentrated on the designated affected area in a state in which the patient is not moving.

In addition, yet another objective of the present disclosure is to provide an apparatus for treating cancer with high-frequency hyperthermia using an angle-adjustable parabolic-shaped rotating high-frequency radiating body electrode, the apparatus being configured such that a frequency and an output level of a high-frequency signal output from the high-frequency radiating body configured to radiate the high-frequency signal to an affected area of a patient are adjusted according to a size of the affected area and a depth which is measured from the skin or which is expected, thereby increasing the treatment effect.

In addition, yet another objective of the present disclosure is to provide an apparatus for treating cancer with high-frequency hyperthermia using an angle-adjustable parabolic-shaped rotating high-frequency radiating body electrode, the apparatus being configured such that a color light signal output device is mounted adjacent to the high-frequency radiating body electrode configured to radiate a high-frequency signal to an affected area of a patient so that a position where the high-frequency signal is concentrated is visually checked, thereby adjusting or controlling the high-frequency signal to be accurately radiated to a checked position of the affected area.

The objectives and various advantages of the present disclosure will be further clarified from an exemplary embodiment of the present disclosure by persons skilled in the art.

In order to achieve the objectives described above, according to a first embodiment of the present disclosure, there is provided an apparatus for treating cancer with high-frequency hyperthermia using an angle-adjustable parabolic-shaped rotating high-frequency radiating body electrode, the apparatus including: an upper end adjustment high-frequency radiating part 1000 fixed to and mounted on an upper side portion of a treatment bed 3000 on which a patient 950 is lying, the upper end adjustment high-frequency radiating part 1000 being configured to move an upper end dish-shaped radiating part 4100 in up and down directions and front, rear, left, and right directions and being configured to adjust an angle at which a high-frequency signal is radiated and being configured to respond with a controlled result, the upper end dish-shaped radiating part 4100 being configured to output a high-frequency signal at a frequency designated by a corresponding control signal to a designated level; and a lower end adjustment high-frequency radiating part 2000 fixed to and mounted on a lower side portion of the treatment bed 3000 corresponding to the upper end adjustment high-frequency radiating part 1000 and embedded inside the treatment bed 3000 on which the patient 950 is lying, the lower end adjustment high-frequency radiating part 2000 being configured to move a lower end dish-shaped radiating part 4200 in the up and down directions and the front, rear, left, and right directions and being configured to adjust an angle at which a high-frequency signal is radiated and being configured to respond with a controlled result, the lower end dish-shaped radiating part 4200 being configured to output a high-frequency signal at a frequency designated by a corresponding control signal to a designated level.

The apparatus may further include a high-frequency treatment management part 5000 connected to the upper end adjustment high-frequency radiating part 1000 and the lower end adjustment high-frequency radiating part 2000, the high-frequency treatment management part 5000 being configured to control, according to an input command signal, a movement position in the up and down directions and the front, rear, left, and right directions of each of the upper end dish-shaped radiating part 4100 and the lower end dish-shaped radiating part 4200 and an angle at which the high-frequency signal is radiated, the high-frequency treatment management part 5000 being configured to analyze and monitor the received result thereof, the high-frequency treatment management part 5000 being configured to control a frequency and a level of the output high-frequency signal, and the high-frequency treatment management part 5000 being configured to analyze and monitor the received result thereof.

The upper end adjustment high-frequency radiating part 1000 may include: the upper end dish-shaped radiating part 4100 configured to output a high-frequency signal at a frequency designated by a corresponding control signal of the high-frequency treatment management part 5000 to a designated level, the upper end dish-shaped radiating part 4100 being configured such that an angle at which a high-frequency signal is radiated frontward is adjusted, and the upper end dish-shaped radiating part 4100 having any one shape selected from a hemispherical parabolic dish shape or a parabolic wing shape formed of at least two parabolic wings; an upper radiating body rotating motor 1010 fixed to and mounted on a rear surface position of the upper end dish-shaped radiating part 4100 where a high-frequency signal of the upper end dish-shaped radiating part 4100 is not radiated, the upper radiating body rotating motor 1010 being configured to be rotated at a designated speed by a corresponding signal of the high-frequency treatment management part 5000; a first upper moving screw bushing 1020 fixed to and mounted on the upper radiating body rotating motor 1010, the first upper moving screw bushing 1020 having a tubular shape and having an inner portion provided with a thread; a first upper screw 1030 screw-coupled to the thread inside the first upper moving screw bushing 1020, the first upper screw 1030 being configured to rectilinearly move the first upper moving screw bushing 1020 in a first direction by being rotated; a first upper sliding guide 1040 fixed to and mounted on a first side end of the first upper screw 1030 such that the first upper sliding guide 1040 is in a rotatable state, the first upper sliding guide 1040 having a tubular shape and having an inner portion thereof hollow; a second upper moving screw bushing 1050 fixed to and mounted on a second side end of the first upper screw 1030 such that the second upper moving screw bushing 1050 is in a rotatable state, the second upper moving screw bushing 1050 having a tubular shape and having an inner portion thereof provided with a thread; a first upper positioning motor 1060 fixed to and mounted on a first side surface of the first upper sliding guide 1040, the first upper positioning motor 1060 being configured to rotate the first upper screw 1030 in a forward direction or a reverse direction by a corresponding control signal of the high-frequency treatment management part 5000; a second upper screw 1070 fixed to and mounted on the second side end of the first upper screw 1030 such that the second upper screw 1070 is in a rotatable state, the second upper screw 1070 being screw-coupled to the thread inside the second upper moving screw bushing 1050, and the second upper screw 1070 being configured to rectilinearly move the second upper moving screw bushing 1050 in a second direction by being rotated; a first upper sliding bar 1080 inserted into and mounted in the tubular shape of the first upper sliding guide 1040, the first upper sliding bar 1080 being configured to guide the first upper sliding guide 1040 to be moved in a sliding state; a second upper positioning motor 1090 connected to and mounted on a second side end of the second upper screw 1070 such that the second upper positioning motor 1090 is in a fixed state, the second upper positioning motor 1090 being configured to rotate the second upper screw 1070 in a forward direction or a reverse direction by a corresponding control signal of the high-frequency treatment management part 5000; a second upper sliding guide 1100 fixed to and mounted on a first side end of the second upper screw 1070 such that the second upper sliding guide 1100 is in a rotatable state, the second upper sliding guide 1100 having a tubular shape and having an inner portion thereof hollow; a second upper sliding bar 1110 inserted into and mounted in the tubular shape of the second upper sliding guide 1100, the second upper sliding bar 1110 being configured to guide the second upper sliding guide 1100 to be moved in a sliding state; a third upper moving screw bushing 1120 fixed to and mounted on a first side end of the first upper sliding bar 1080, the third upper moving screw bushing 1120 having a tubular shape and having an inner portion thereof provided with a thread; a third upper screw 1130 screw-coupled to the thread inside the third upper moving screw bushing 1120, the third upper screw 1130 being configured to rectilinearly move the third upper moving screw bushing 1120 in a third direction by being rotated; a third upper positioning motor 1140 connected to and mounted on a first side end of the third upper screw 1130, the third upper positioning motor 1140 being configured to rotate the third upper screw 1130 in a forward direction or a reverse direction by a corresponding control signal of the high-frequency treatment management part 5000; and an upper frame part 1150 having a hexahedral box shape that forms an external appearance of the upper end adjustment high-frequency radiating part 1000.

The lower end adjustment high-frequency radiating part 2000 may include: the lower end dish-shaped radiating part 4200 configured to output a high-frequency signal at a frequency designated by a corresponding control signal of the high-frequency treatment management part 5000 to a designated level, the lower end dish-shaped radiating part 4200 being configured such that an angle at which a high-frequency signal is radiated frontward is adjusted, and the lower end dish-shaped radiating part 4200 having any one shape selected from a hemispherical parabolic dish shape or a parabolic wing shape formed of at least two parabolic wings; an lower radiating body rotating motor 2010 fixed to and mounted on a rear surface position of the lower end dish-shaped radiating part 4200 where a high-frequency signal of the lower end dish-shaped radiating part 4200 is not radiated, the lower radiating body rotating motor 2010 being configured to be rotated at a designated speed by a corresponding signal of the high-frequency treatment management part 5000; a first lower moving screw bushing 2020 fixed to and mounted on the lower radiating body rotating motor 2010, the first lower moving screw bushing 2020 having a tubular shape and having an inner portion provided with a thread; a first lower screw 2030 screw-coupled to the thread inside the first lower moving screw bushing 2020, the first lower screw 2030 being configured to rectilinearly move the first lower moving screw bushing 2020 in a first direction by being rotated; a first lower sliding guide 2040 fixed to and mounted on a first side end of the first lower screw 2030 such that the first lower sliding guide 2040 is in a rotatable state, the first lower sliding guide 2040 having a tubular shape and having an inner portion thereof hollow; a second lower moving screw bushing 2050 fixed to and mounted on a second side end of the first lower screw 2030 such that the second lower moving screw bushing 2050 is in a rotatable state, the second lower moving screw bushing 2050 having a tubular shape and having an inner portion thereof provided with a thread; a first lower positioning motor 2060 fixed to and mounted on a first side surface of the first lower sliding guide 2040, the first lower positioning motor 2060 being configured to rotate the first lower screw 2030 in a forward direction or a reverse direction by a corresponding control signal of the high-frequency treatment management part 5000; a second lower screw 2070 fixed to and mounted on the second side end of the first lower screw 2030 such that the second lower screw 2070 is in a rotatable state, the second lower screw 2070 being screw-coupled to the thread inside the second lower moving screw bushing 2050, and the second lower screw 2070 being configured to rectilinearly move the second lower moving screw bushing 2050 in a second direction by being rotated; a first lower sliding bar 2080 inserted into and mounted in the tubular shape of the first lower sliding guide 2040, the first lower sliding bar 2080 being configured to guide the first lower sliding guide 2040 to be moved in a sliding state;

a second lower positioning motor 2090 connected to and mounted on a second side end of the second lower screw 2070 such that the second lower positioning motor 2090 is in a fixed state, the second lower positioning motor 2090 being configured to rotate the second lower screw 2070 in a forward direction or a reverse direction by a corresponding control signal of the high-frequency treatment management part 5000; a second lower sliding guide 2100 fixed to and mounted on a first side end of the second lower screw 2070 such that the second lower sliding guide 2100 is in a rotatable state, the second lower sliding guide 2100 having a tubular shape and having an inner portion thereof hollow; a second lower sliding bar 2110 inserted into and mounted in the tubular shape of the second lower sliding guide 2100, the second lower sliding bar 2110 being configured to guide the second lower sliding guide 2100 to be moved in a sliding state; a third lower moving screw bushing 2120 fixed to and mounted on a first side end of the first lower sliding bar 2080, the third lower moving screw bushing 2120 having a tubular shape and having an inner portion thereof provided with a thread; a third lower screw 2130 screw-coupled to the thread inside the third lower moving screw bushing 2120, the third lower screw 2130 being configured to rectilinearly move the third lower moving screw bushing 2120 in a third direction by being rotated; a third lower positioning motor 2140 connected to and mounted on a first side end of the third lower screw 2130, the third lower positioning motor 2140 being configured to rotate the third lower screw 2130 in a forward direction or a reverse direction by a corresponding control signal of the high-frequency treatment management part 5000; and a lower frame part 2150 having a hexahedral box shape that forms an external appearance of the lower end adjustment high-frequency radiating part 2000.

The high-frequency treatment management part 5000 may include: a high-frequency hyperthermia treatment management part 5010 configured to monitor, according to embedded data and an input command signal, an overall operation of the apparatus 900 for treating cancer with high-frequency hyperthermia using the angle-adjustable parabolic-shaped rotating high-frequency radiating body electrode, the high-frequency hyperthermia treatment management part 5010 being configured to output a corresponding control signal to each of the upper end adjustment high-frequency radiating part 1000 and the lower end adjustment high-frequency radiating part 2000; a high-frequency signal generation part 5020 connected to the high-frequency hyperthermia treatment management part 5010, the high-frequency signal generation part 5020 being configured to generate and adjust a frequency and an output level of a high-frequency signal radiated from each of the upper end adjustment high-frequency radiating part 1000 and the lower end adjustment high-frequency radiating part 2000 according to the corresponding control signal; a positioning motor operation control part 5030 connected to the high-frequency hyperthermia treatment management part 5010, the positioning motor operation control part 5030 being configured to control and monitor a rotation speed and a rotation time of each positioning motor provided on each of the upper end adjustment high-frequency radiating part 1000 and the lower end adjustment high-frequency radiating part 2000 according to the corresponding control signal; an affected area size treatment information table 5040 connected to the high-frequency hyperthermia treatment management part 5010, the affected area size treatment information table 5040 being configured to record a frequency, an output level, and an output time of the high-frequency signal corresponding to a position and a size of an affected area as a table according to the corresponding control signal, and the affected area size treatment information table 5040 being configured to output the information through retrieval and to manage updates; a radiating body angle management part 5050 connected to the high-frequency hyperthermia treatment management part 5010, the radiating body angle management part 5050 being configured to control and monitor a radiating angle of the high-frequency signal from each of the upper end dish-shaped radiating part 4100 and the lower end dish-shaped radiating part 4200 provided on each of the upper end adjustment high-frequency radiating part 1000 and the lower end adjustment high-frequency radiating part 2000 according to the corresponding control signal; a treatment information real-time recording part 5060 connected to the high-frequency hyperthermia treatment management part 5010, the treatment information real-time recording part 5060 being configured to record and manage in real time the corresponding control signal applied to the upper end adjustment high-frequency radiating part 1000 and the lower end adjustment high-frequency radiating part 2000 along with a received result signal in association with time information; and an external input/output communication part 5070 connected to the high-frequency hyperthermia treatment management part 5010, the external input/output communication part 5070 being configured to input a command signal and to output data according to the corresponding control signal by being in communication with the outside.

The upper end dish-shaped radiating part 4100 may include: a mounting and fixing origin part 4101 which is formed at a center of the upper end dish-shaped radiating part 4100 and which is a center of a fixing and mounting position; a first base part 4103 having a center provided with the mounting and fixing origin part 4101, the first base part 4103 being provided as at least two first base parts 4103 or being formed in a hemispherical parabolic dish shape; a first high-frequency signal element 4105 mounted on the first base part 4103, the first high-frequency signal element 4105 being configured to output a high-frequency signal at a designated frequency and a designated output level by a corresponding control signal of the high-frequency treatment management part 5000, and the first high-frequency signal element 4105 being provided as at least two first high-frequency signal elements 4105; a first hinge part 4107 mounted on a border portion of the first base part 4103, the first hinge part 4107 being hinge-coupled to a second base part 4109; the second base part 4109 connected to and mounted on an outer portion of the first base part 4103 in a rotatable state by the first hinge part 4107, the second base part 4109 being provided as at least two second base parts 4109 or being formed in a hemispherical parabolic dish shape; a second high-frequency signal element 4111 mounted on the second base part 4109, the second high-frequency signal element 4111 being configured to output a high-frequency signal at a designated frequency and a designated output level by a corresponding control signal of the high-frequency treatment management part 5000, and the second high-frequency signal element 4111 being provided as at least two second high-frequency signal elements 4111; an angle adjustment piston 4113 having a first side end thereof fixed to and mounted on a first side portion of the first base part 4103, the angle adjustment piston 4113 having a length thereof configured to extend or contract by a corresponding control signal of the high-frequency treatment management part 5000; a second hinge part 4115 fixed to and mounted on a first side portion of the second base part 4109, the second hinge part 4115 being hinge-coupled to a second side end of the angle adjustment piston 4113; and a color light generation part 4117 mounted adjacent to the second high-frequency signal element 4111 of the second base part 4109, the color light generation part 4117 being configured such that a light signal of a red color or a selected color is output by a corresponding control signal of the high-frequency treatment management part 5000.

The lower end dish-shaped radiating part 4200 may include: a lower end mounting and fixing origin part 4201 which is formed at a center of the lower end dish-shaped radiating part 4200 and which is a center of a fixing and mounting position and a rotation center; a first lower end base part 4203 having a center provided with the lower end mounting and fixing origin part 4201, the first lower end base part 4203 being provided as at least two first base parts 4203 or being formed in a hemispherical parabolic dish shape; a first lower end high-frequency signal element 4205 mounted on the first lower end base part 4203, the first lower end high-frequency signal element 4205 being configured to output a high-frequency signal at a designated frequency and a designated output level by a corresponding control signal of the high-frequency treatment management part 5000, and the first lower end high-frequency signal element 4205 being provided as at least two first lower end high-frequency signal elements 4205; a first lower end hinge part 4207; a second lower end base part 4209 connected to and mounted on an outer portion of the first lower end base part 4203 in a rotatable state by the first lower end hinge part 4207, the second lower end base part 4209 being provided as at least two second lower end base parts 4209 or being formed in a hemispherical parabolic dish shape; a second lower end high-frequency signal element 4211 mounted on the second lower end base part 4209, the second lower end high-frequency signal element 4211 being configured to output a high-frequency signal at a designated frequency and a designated output level by a corresponding control signal of the high-frequency treatment management part 5000, and the second lower end high-frequency signal element 4211 being provided as at least two second lower end high-frequency signal elements 4211; a lower end angle adjustment piston 4213 having a first side end thereof fixed to and mounted on a first side portion of the first lower end base part 4203, the lower end angle adjustment piston 4213 having a length thereof configured to extend or contract by a corresponding control signal of the high-frequency treatment management part 5000; a second lower end hinge part 4215 fixed to and mounted on a first side portion of the second lower end base part 4209, the second lower end hinge part 4215 being hinge-coupled to a second side end of the lower end angle adjustment piston 4213; and a lower end color light generation part 4217 mounted adjacent to the second lower end high-frequency signal element 4211 of the second lower end base part 4209, the lower end color light generation part 4217 being configured such that a light signal of a red color or a selected color is output by a corresponding control signal of the high-frequency treatment management part 5000.

In order to achieve the objectives described above, according to a second embodiment of the present disclosure, there is provided an apparatus for treating cancer with high-frequency hyperthermia using an angle-adjustable parabolic-shaped rotating high-frequency radiating body electrode, the apparatus including: an upper end adjustment high-frequency radiating part 1000 fixed to and mounted on an upper side portion of a treatment bed 3000 on which a patient 950 is lying, the upper end adjustment high-frequency radiating part 1000 being configured to move an upper end dish-shaped radiating part 4100' in up and down directions and front, rear, left, and right directions and being configured to adjust an angle at which a high-frequency signal is radiated and being configured to respond with a controlled result, the upper end dish-shaped radiating part 4100' being configured to output a high-frequency signal at a frequency designated by a corresponding control signal to a designated level; and a lower end adjustment high-frequency radiating part 2000 fixed to and mounted on a lower side portion of the treatment bed 3000 corresponding to the upper end adjustment high-frequency radiating part 1000 and embedded inside the treatment bed 3000 on which the patient 950 is lying, the lower end adjustment high-frequency radiating part 2000 being configured to move a lower end dish-shaped radiating part 4200' in the up and down directions and the front, rear, left, and right directions and being configured to adjust an angle at which a high-frequency signal is radiated and being configured to respond with a controlled result, the lower end dish-shaped radiating part 4200' being configured to output a high-frequency signal at a frequency designated by a corresponding control signal to a designated level.

The upper end adjustment high-frequency radiating part 1000 may include: the upper end dish-shaped radiating part 4100' configured to output a high-frequency signal at a frequency designated by a corresponding control signal of to a designated level, the upper end dish-shaped radiating part 4100' being configured such that an angle at which a high-frequency signal is radiated frontward is adjusted, and the upper end dish-shaped radiating part 4100' having any one shape selected from a hemispherical parabolic dish shape or a parabolic wing shape formed of at least two parabolic wings; a first upper moving screw bushing 1020 fixed to and mounted on the upper end dish-shaped radiating part 4100', the first upper moving screw bushing 1020 having a tubular shape in which a center in a longitudinal direction thereof is penetrated, and the first upper moving screw bushing 1020 having an inner portion thereof provided with a thread; a first upper screw 1030 screw-coupled to the thread inside the first upper moving screw bushing 1020, the first upper screw 1030 being configured to rectilinearly move the first upper moving screw bushing 1020 in a first direction by being rotated; a first upper sliding guide 1040 fixed to and mounted on a first side end of the first upper screw 1030 such that the first upper sliding guide 1040 is in a rotatable state, the first upper sliding guide 1040 having a tubular shape and having an inner portion thereof hollow; a second upper moving screw bushing 1050 fixed to and mounted on a second side end of the first upper screw 1030 such that the second upper moving screw bushing 1050 is in a rotatable state, the second upper moving screw bushing 1050 having a tubular shape and having an inner portion thereof provided with a thread; a first upper positioning motor 1060 fixed to and mounted on a first side surface of the first upper sliding guide 1040, the first upper positioning motor 1060 being configured to rotate the first upper screw 1030 in a forward direction or a reverse direction by a corresponding control signal; and a second upper screw 1070 fixed to and mounted on the second side end of the first upper screw 1030 such that the second upper screw 1070 is in a rotatable state, the second upper screw 1070 being screw-coupled to the thread inside the second upper moving screw bushing 1050, and the second upper screw 1070 being configured to rectilinearly move the second upper moving screw bushing 1050 in a second direction by being rotated.

The upper end adjustment high-frequency radiating part 1000 may include: a first upper sliding bar 1080 inserted into and mounted in the tubular shape of the first upper sliding guide 1040, the first upper sliding bar 1080 being configured to guide the first upper sliding guide 1040 to be moved in a sliding state; a second upper positioning motor 1090 connected to and mounted on a second side end of the second upper screw 1070 such that the second upper positioning motor 1090 is in a fixed state, the second upper positioning motor 1090 being configured to rotate the second upper screw 1070 in a forward direction or a reverse direction by a corresponding control signal; a second upper sliding guide 1100 fixed to and mounted on a first side end of the second upper screw 1070 such that the second upper sliding guide 1100 is in a rotatable state, the second upper sliding guide 1100 having a tubular shape and having an inner portion thereof hollow; a second upper sliding bar 1110 inserted into and mounted in the tubular shape of the second upper sliding guide 1100, the second upper sliding bar 1110 being configured to guide the second upper sliding guide 1100 to be moved in a sliding state; a third upper moving screw bushing 1120 fixed to and mounted on a first side end of the first upper sliding bar 1080, the third upper moving screw bushing 1120 having a tubular shape and having an inner portion thereof provided with a thread; a third upper screw 1130 screw-coupled to the thread inside the third upper moving screw bushing 1120, the third upper screw 1130 being configured to rectilinearly move the third upper moving screw bushing 1120 in a third direction by being rotated; a third upper positioning motor 1140 connected to and mounted on a first side end of the third upper screw 1130, the third upper positioning motor 1140 being configured to rotate the third upper screw 1130 in a forward direction or a reverse direction by a corresponding control signal; and an upper frame part 1150 having a hexahedral box shape that forms an external appearance of the upper end adjustment high-frequency radiating part 1000.

The upper end dish-shaped radiating part 4100' may include: a mounting and fixing origin part 4101 which is formed at a center of the upper end dish-shaped radiating part 4100' and which is a center of a fixing and mounting position; a first base part 4103 having a center provided with the mounting and fixing origin part 4101, the first base part 4103 being provided as at least two first base parts 4103 or being formed in a hemispherical parabolic dish shape; and a first high-frequency signal element 4105 mounted on the first base part 4103, the first high-frequency signal element 4105 being configured to output a high-frequency signal at a designated frequency and a designated output level by a corresponding control signal of a high-frequency treatment management part 5000', and the first high-frequency signal element 4105 being provided as at least two first high-frequency signal elements 4105.

In the present disclosure having the configuration described above, since a cross-sectional area of the high-frequency radiating body electrode configured to radiate a high-frequency signal to the affected area of the patient is formed in a curved shape of a parabola, the generated high-frequency signal is concentrated on a specific position, so that there is an advantage that the treatment effect is increased.

In addition, in the present disclosure, since the high-frequency radiating body electrode configured to radiate a high-frequency signal to the affected area of the patient is formed in any one shape selected from the parabolic wing shape or the parabolic hemispherical shape, the extent to which the high-frequency signal is concentrated is adjusted, so that there is an advantage that the treatment effect is increased.

Meanwhile, in the present disclosure, since the position of the high-frequency radiating body electrode configured to radiate the high-frequency signal to the affected area of the patient is moved in the up and down directions and the front, rear, left, and right directions, there is an advantage that the radiation of the high-frequency signal to the designated affected area is easily performed in a state in which the patient is not moving.

In addition, in the present disclosure, since the frequency and the output level of the high-frequency signal output from the high-frequency radiating body configured to radiate the high-frequency signal to the affected area of the patient are adjusted according to the size of the affected area and the depth which is measured from the skin or which is expected, there is an advantage that the treatment effect is increased.

In addition, in the present disclosure, since the color light signal output device is mounted adjacent to the high-frequency radiating body electrode configured to radiate the high-frequency signal to the affected area of the patient so that a position where the high-frequency signal is concentrated is visually checked, so that there is an advantage that the high-frequency signal is accurately radiated to a checked position of the affected area.

BRIEF DESCRIPTION OF THE DRAWINGS

The above and other objectives, features, and other advantages of the present disclosure will be more clearly understood from the following detailed description when taken in conjunction with the accompanying drawings, in which.

DETAILED DESCRIPTION

Figure 1:
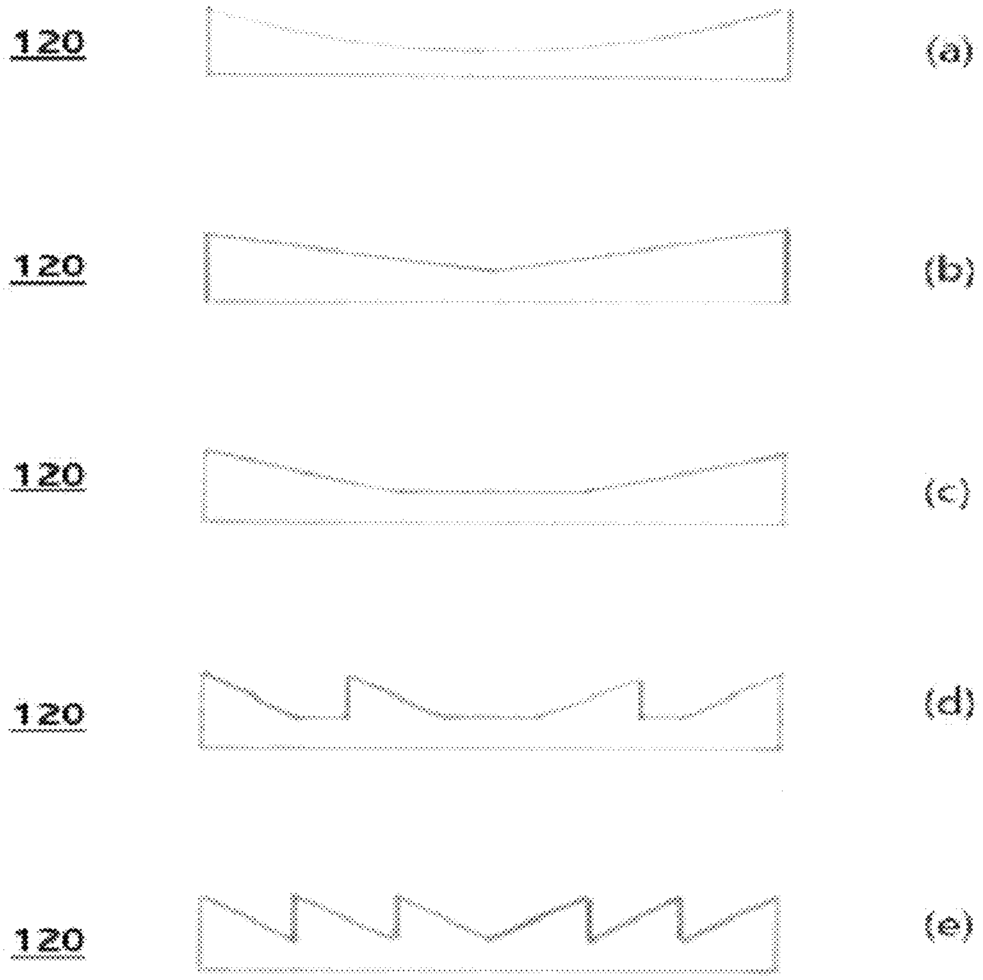
FIG. 1 is a view illustrating a functional configuration of an apparatus for treating cancer with high-frequency hyperthermia according to an embodiment of a conventional technology.

Since the present disclosure may be variously changed and have various embodiments, particular embodiments will be exemplified in the drawings and will be described in detail in the detailed description. It should be understood, however, that the present disclosure is not intended to be limited to the specific embodiments, but the present disclosure includes all modifications, equivalents or replacements that fall within the spirit and scope of the disclosure as defined in the following claims. In describing the present disclosure, a detailed description of known technologies will be omitted when it may obscure the subject matter of the present disclosure.

Hereinafter, "injection", "infusion", "irradiation", and "radiation" are used interchangeably to convey the same meaning, and "control" and "adjustment" are also used interchangeably. Each term is selectively and appropriately used according to the context.

In addition, the numbers assigned to each functional component described hereinafter are used to explain the technical concept and the functional configuration, and such numbers may be depicted and described as limited for the sake of clarity and ease of understanding. However, it is evident that these numbers may be increased or decreased as required.

In addition, the attached drawings may be exaggerated since the drawings are illustrated for the purpose of describing the function.

Figure 2:
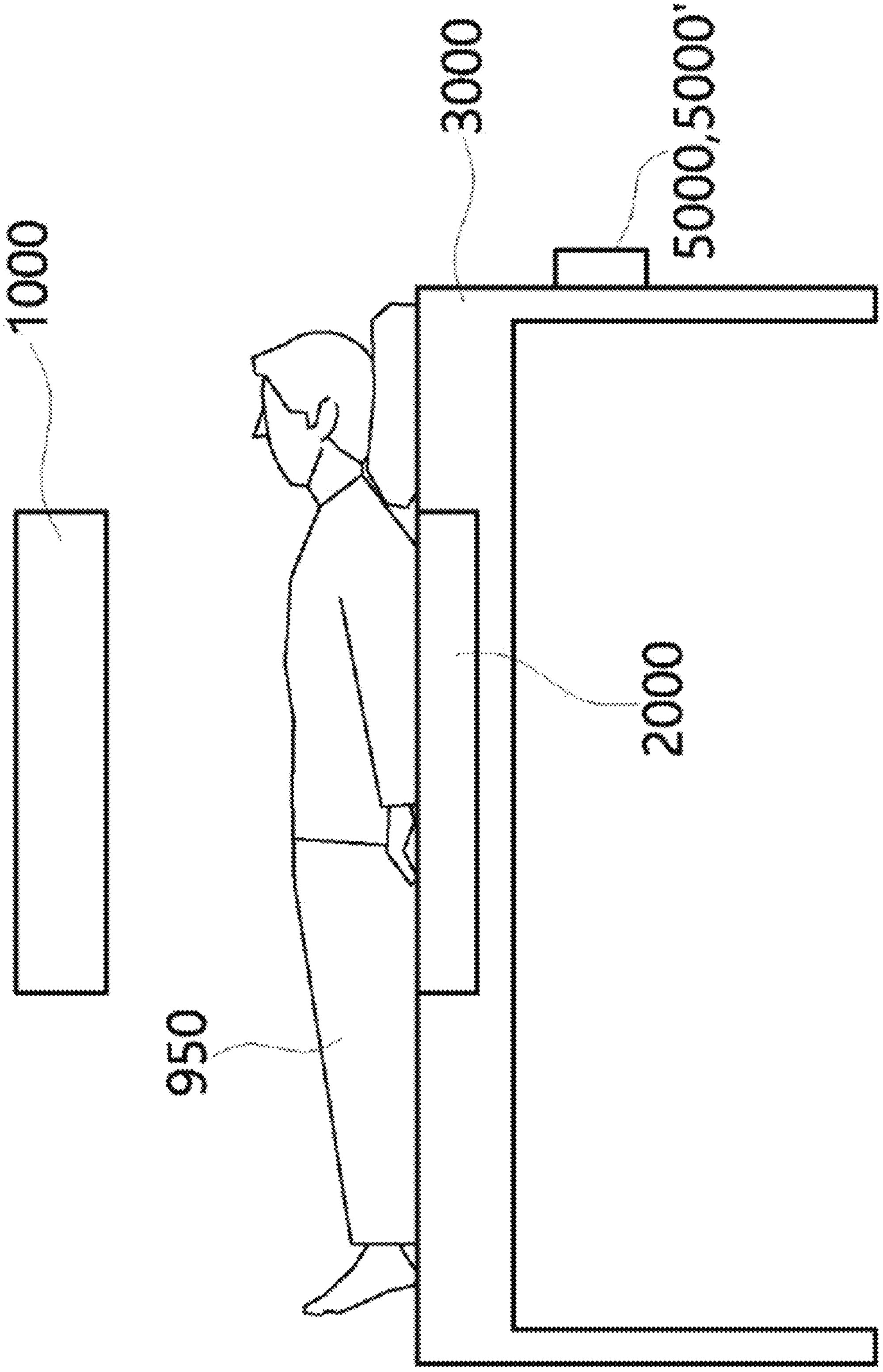
FIG. 2 is a view illustrating a state of use of an apparatus for treating cancer with high-frequency hyperthermia using an angle-adjustable parabolic-shaped rotating high-frequency radiating body electrode according to an embodiment of the present disclosure.
Figure 3:
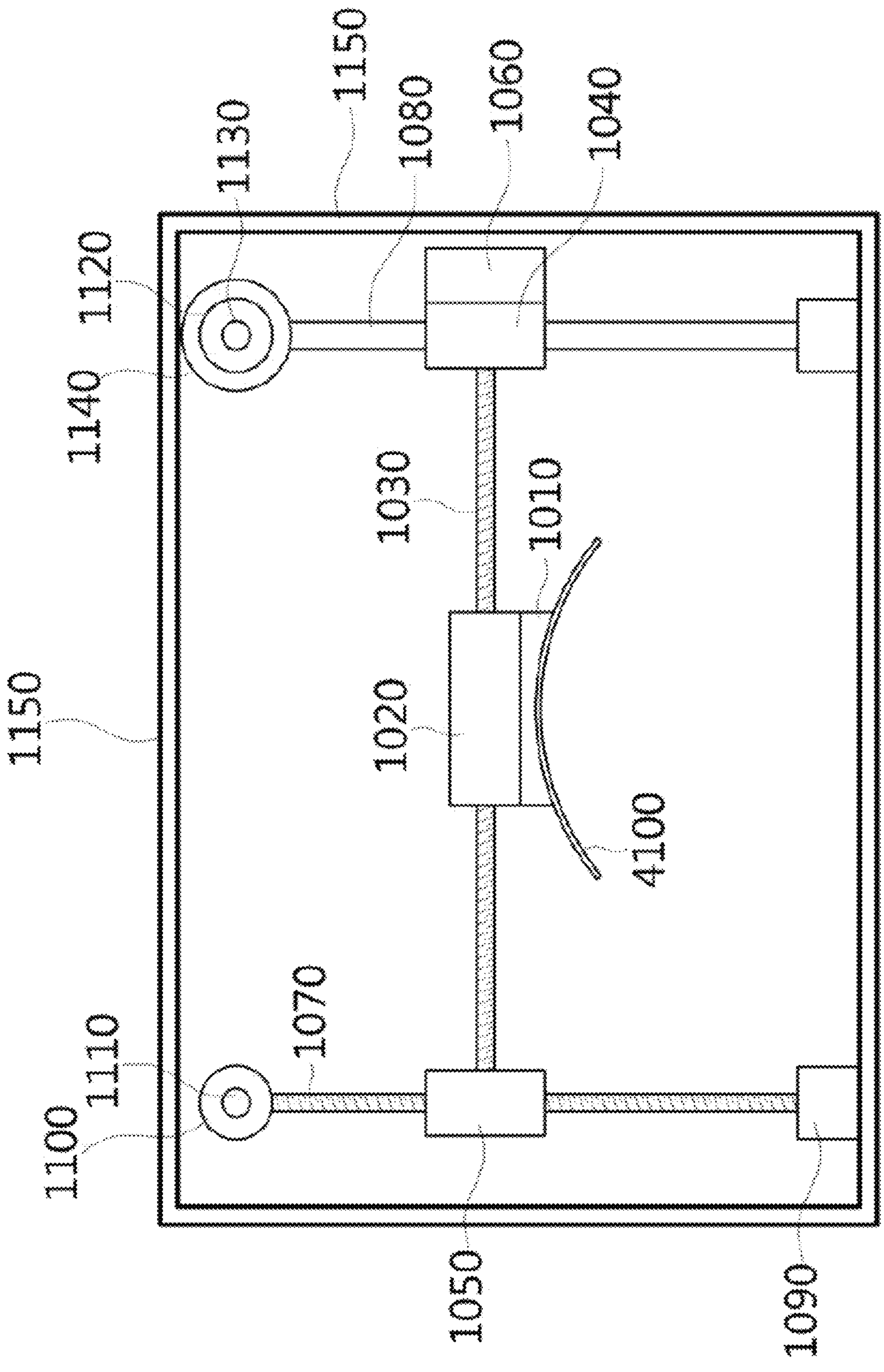
FIG. 3 is a view illustrating a detailed functional configuration of an upper end adjustment high-frequency radiating part according to an embodiment of the present disclosure.
Figure 4:
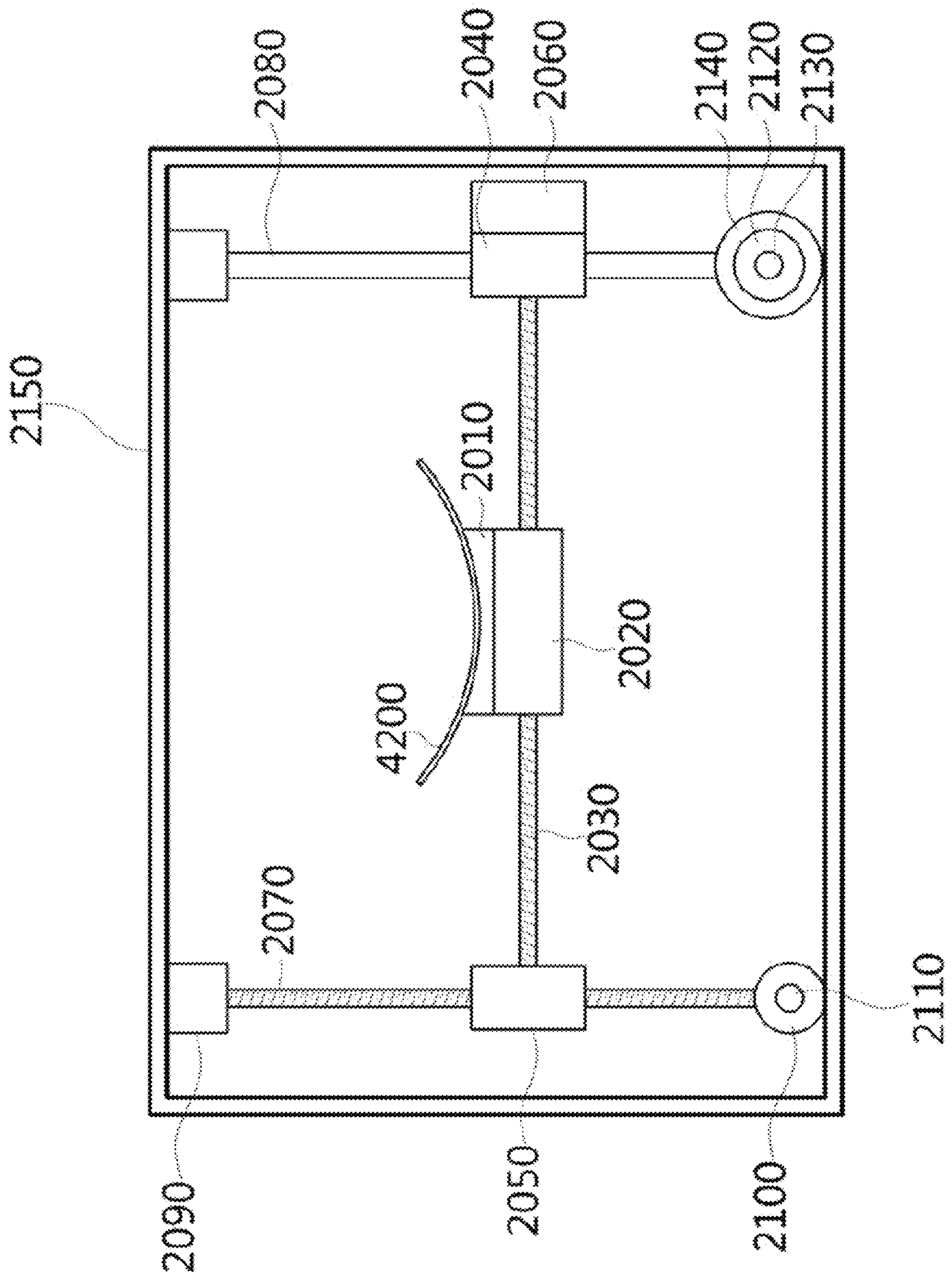
FIG. 4 is a view illustrating a detailed functional configuration of a lower end adjustment high-frequency radiating part according to an embodiment of the present disclosure.
Figure 5:
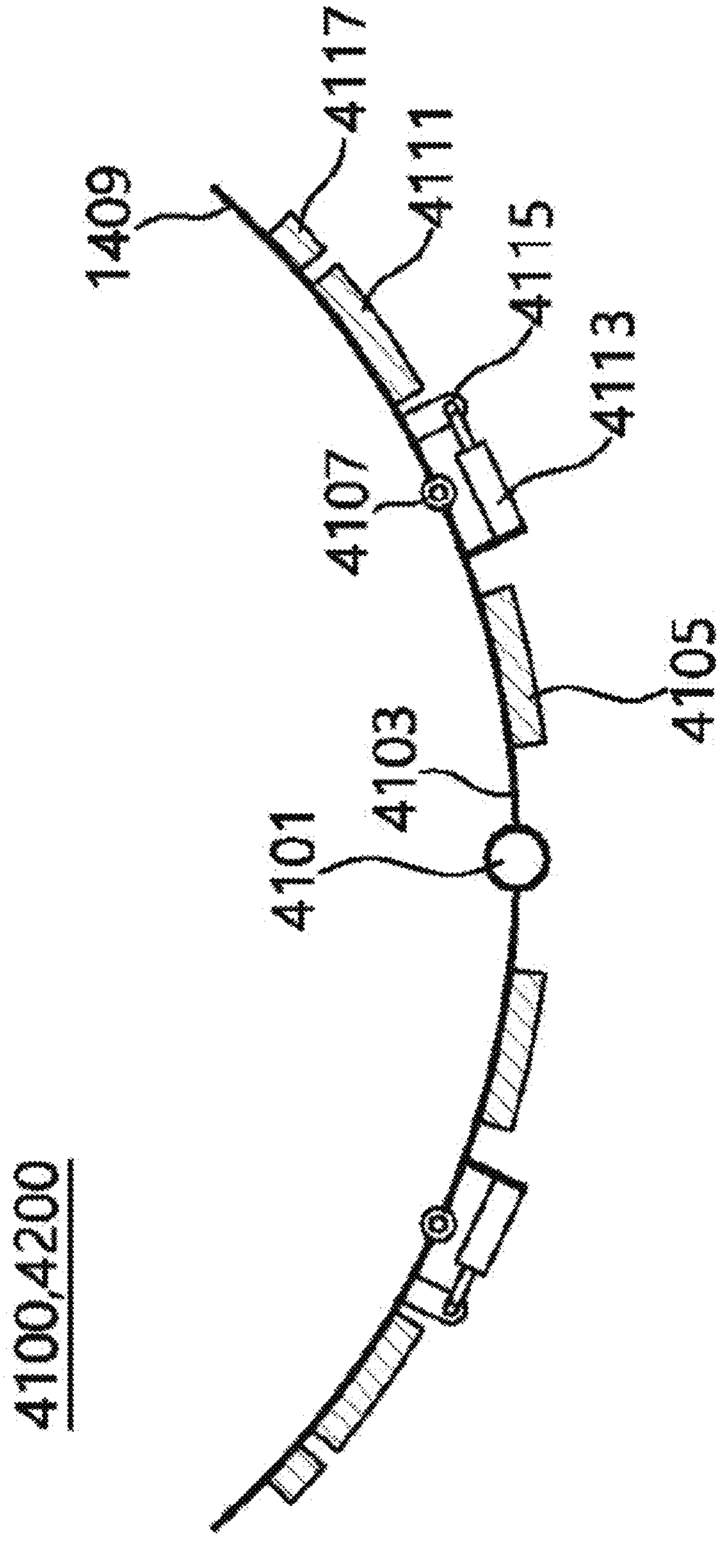
FIG. 5 is a view illustrating a cross-sectional configuration of a dish-shaped radiating part according to a first embodiment of the present disclosure.
Figure 6:
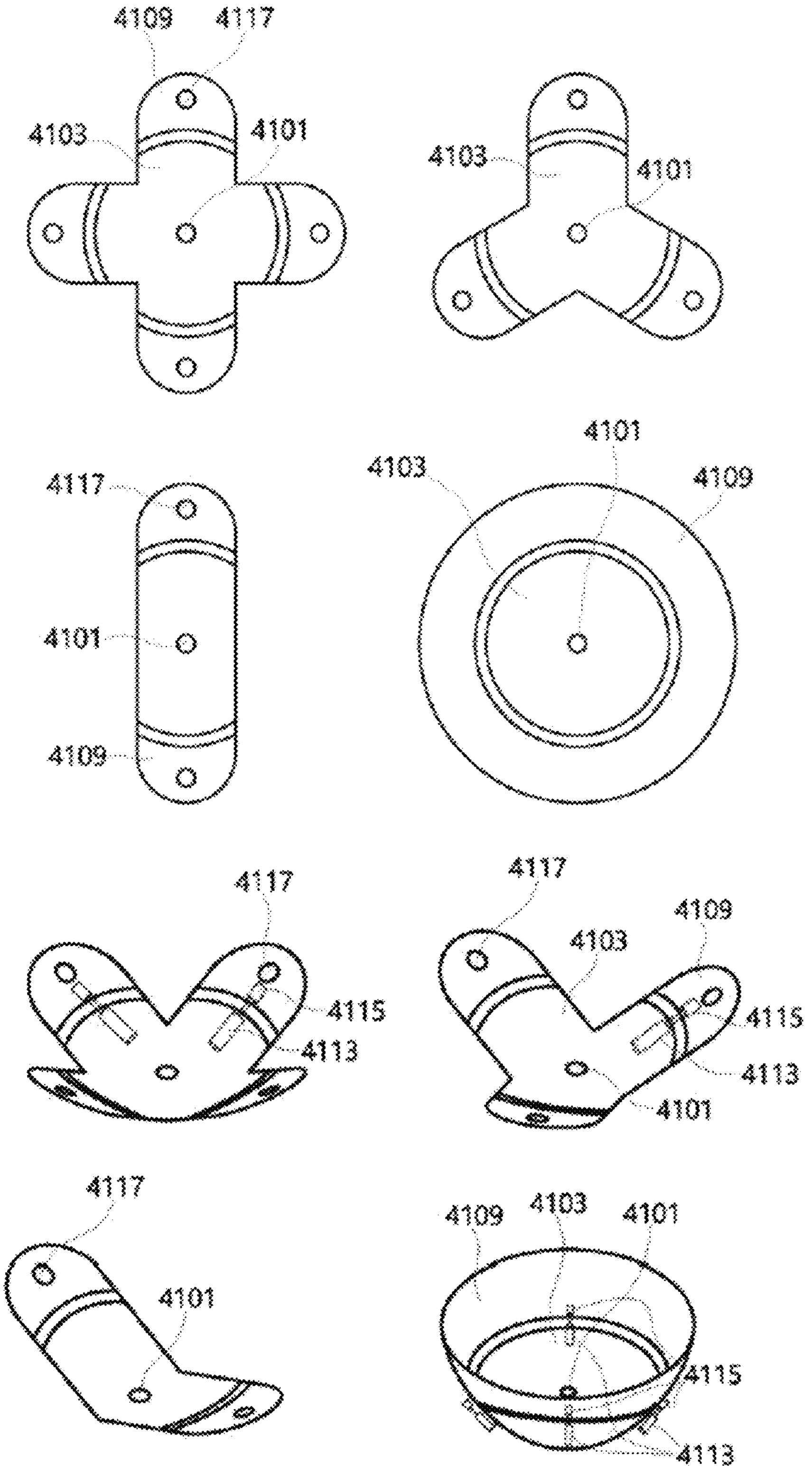
FIG. 6 is a view illustrating various shapes of the dish-shaped radiating part according to the first embodiment of the present disclosure.
Figure 7:
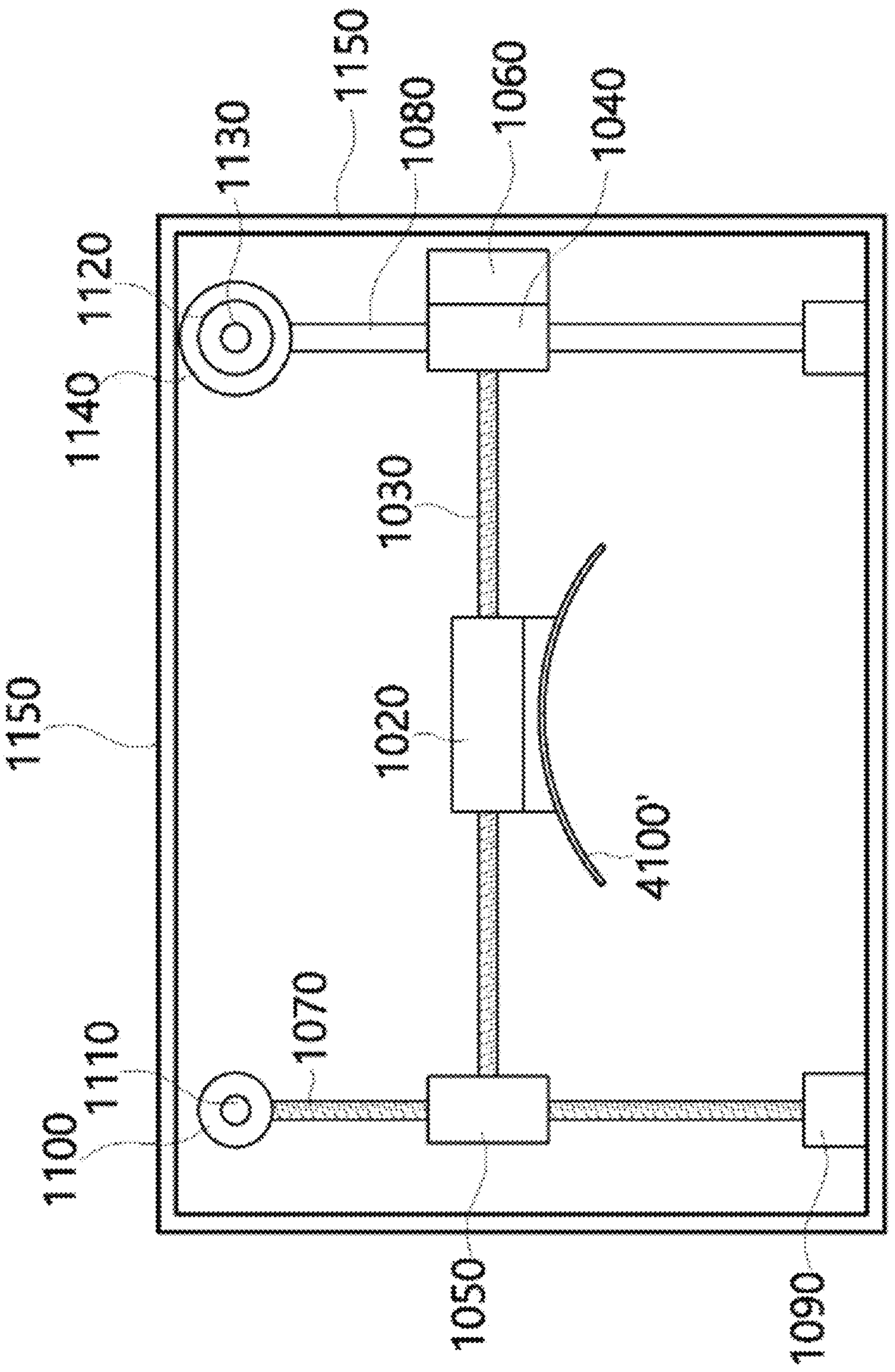
FIG. 7 is a view illustrating a detailed functional configuration of the upper end adjustment high-frequency radiating part according to a second embodiment of the present disclosure.
Figure 8:
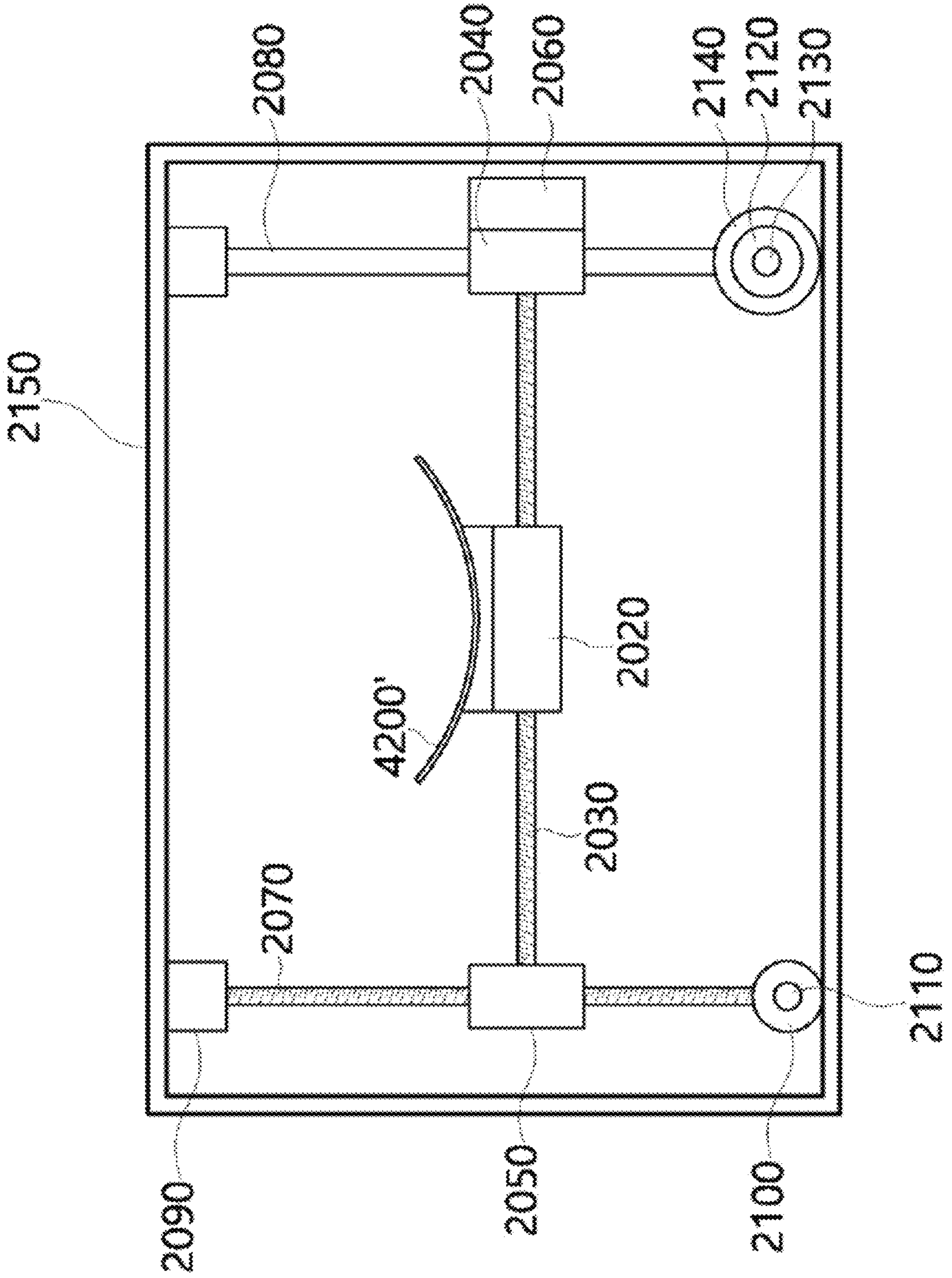
FIG. 8 is a view illustrating a detailed functional configuration of the lower end adjustment high-frequency radiating part according to the second embodiment of the present disclosure.
Figure 9:
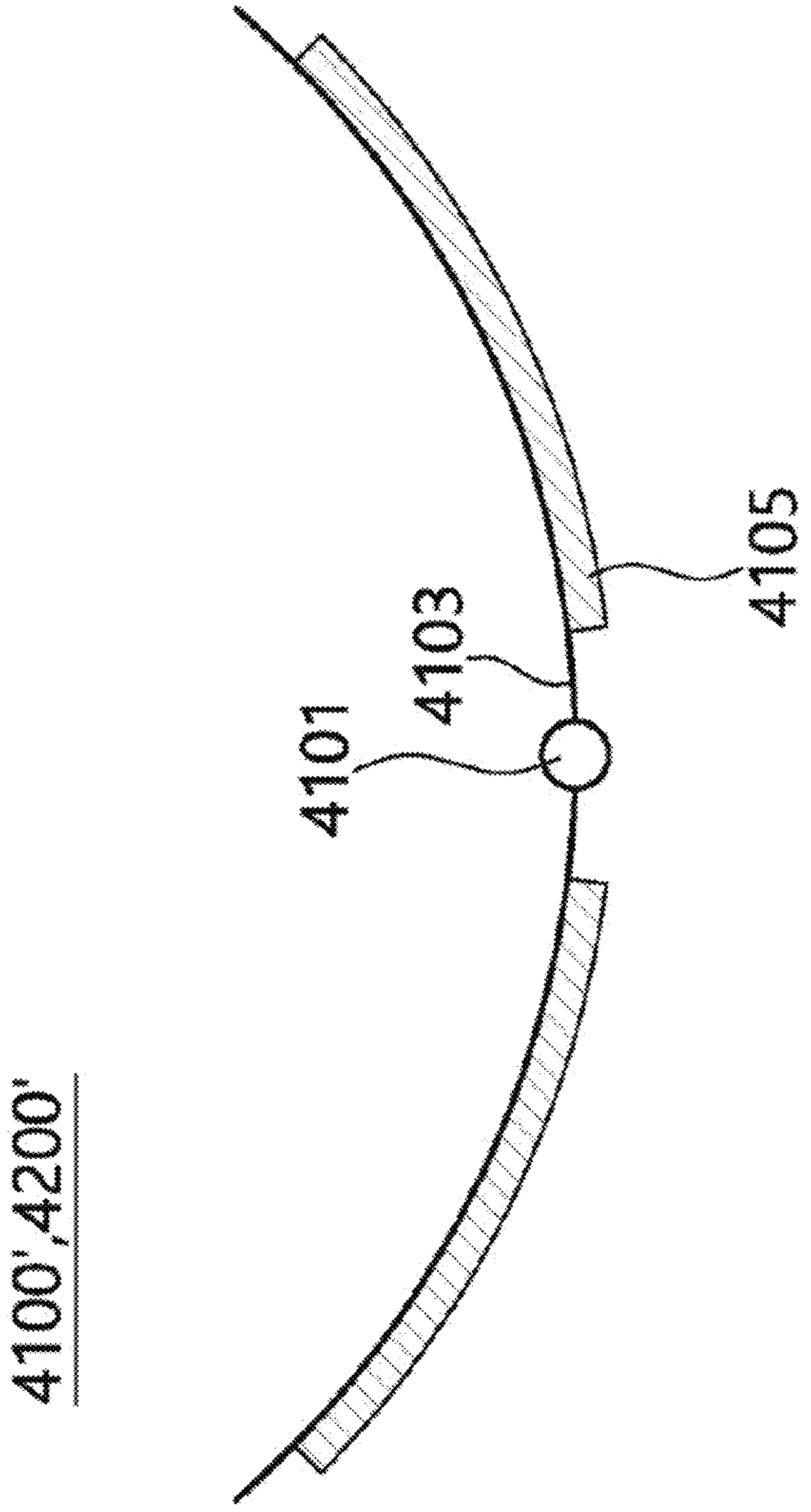
FIG. 9 is a view illustrating a cross-sectional configuration of the dish-shaped radiating part according to the second embodiment of the present disclosure.
Figure 10:
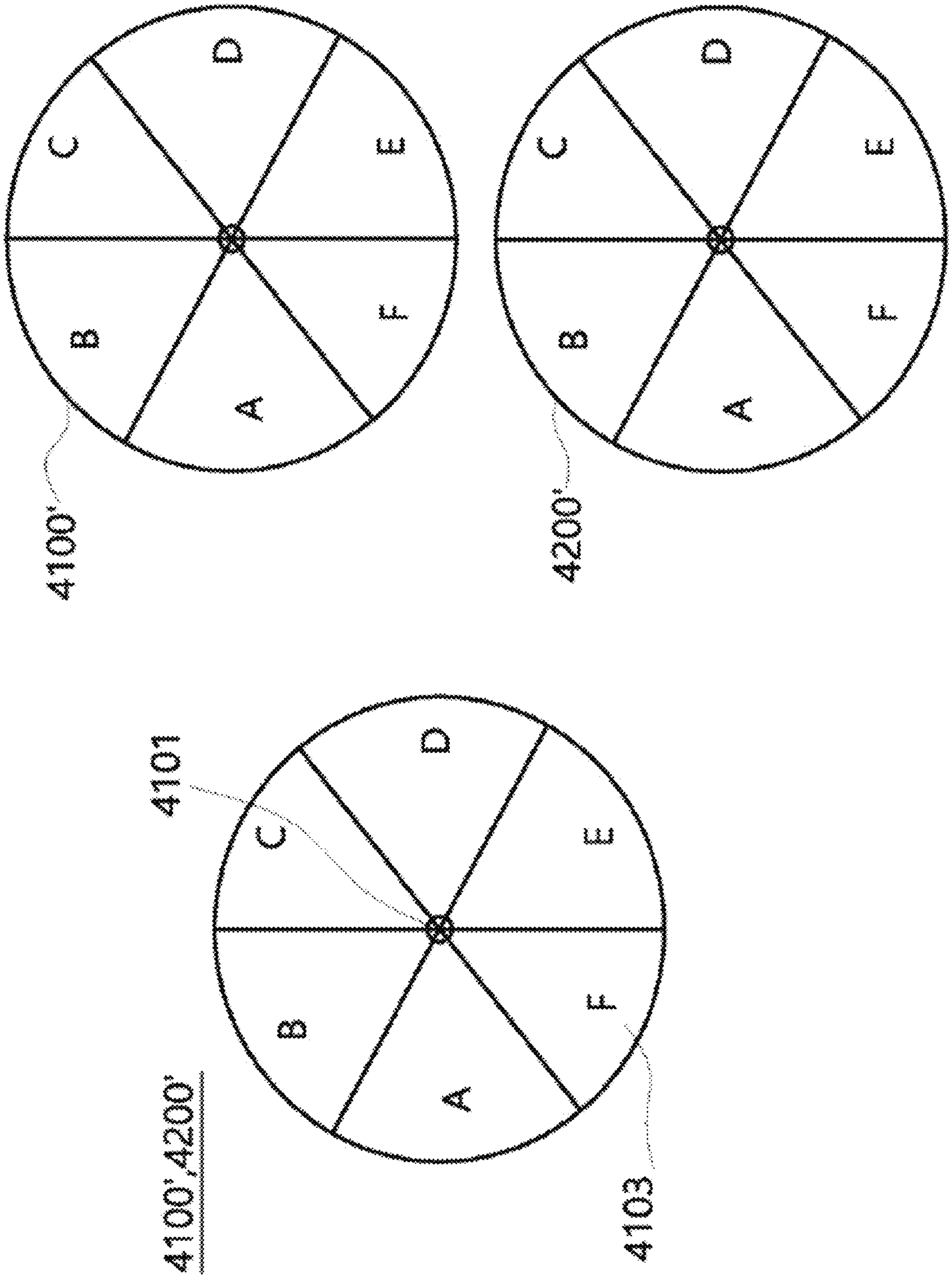
FIG. 10 is a reference view illustrating a planar arrangement configuration and an operation method of the dish-shaped radiating part.
Figure 11:
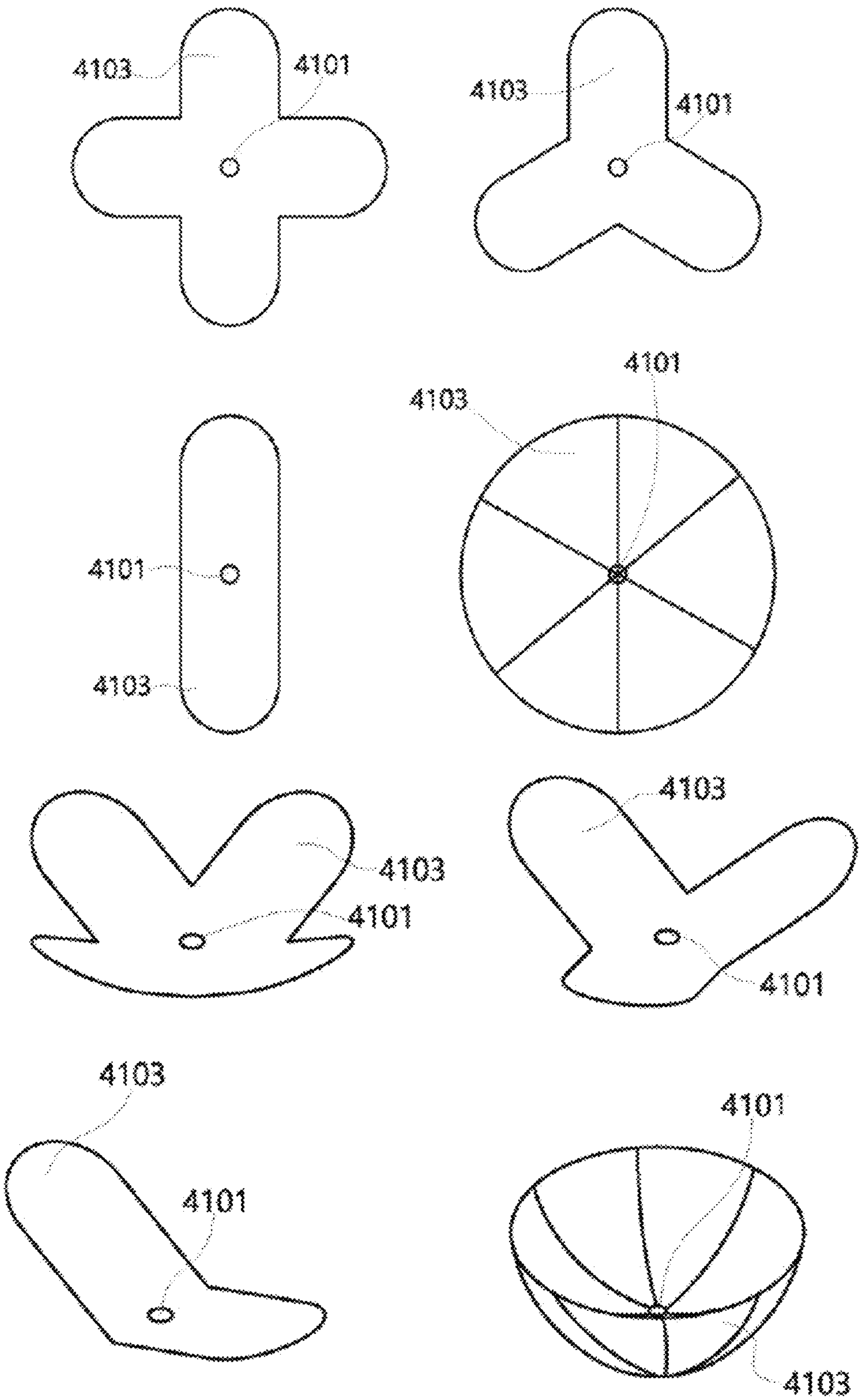
FIG. 11 is a view illustrating various shapes of the dish-shaped radiating part according to the second embodiment of the present disclosure.

FIG. 2 is a view illustrating a state of use of an apparatus for treating cancer with high-frequency hyperthermia using an angle-adjustable parabolic-shaped rotating high-frequency radiating body electrode according to an embodiment of the present disclosure, FIG. 3 is a view illustrating a detailed functional configuration of an upper end adjustment high-frequency radiating part according to an embodiment of the present disclosure, FIG. 4 is a view illustrating a detailed functional configuration of a lower end adjustment high-frequency radiating part according to an embodiment of the present disclosure, FIG. 5 is a view illustrating a cross-sectional configuration of a dish-shaped radiating part according to a first embodiment of the present disclosure, FIG. 6 is a view illustrating various shapes of the dish-shaped radiating part according to the first embodiment of the present disclosure, FIG. 7 is a view illustrating a detailed functional configuration of the upper end adjustment high-frequency radiating part according to a second embodiment of the present disclosure, FIG. 8 is a view illustrating a detailed functional configuration of the lower end adjustment high-frequency radiating part according to the second embodiment of the present disclosure, FIG. 9 is a view illustrating a cross-sectional configuration of the dish-shaped radiating part according to the second embodiment of the present disclosure, FIG. 10 is a reference view illustrating a planar arrangement configuration and an operation method of the dish-shaped radiating part; and FIG. 11 is a view illustrating various shapes of the dish-shaped radiating part according to the second embodiment of the present disclosure.

Hereinafter, referring to all the accompanying drawings, an apparatus 900 for treating cancer with high-frequency hyperthermia using an angle-adjustable parabolic-shaped rotating high-frequency radiating body electrode according to a first embodiment of the present disclosure will be described. The apparatus 900 for treating cancer with high-frequency hyperthermia using the angle-adjustable parabolic-shaped rotating high-frequency radiating body electrode according to the first embodiment of the present disclosure includes an upper end adjustment high-frequency radiating part 1000, a lower end adjustment high-frequency radiating part 2000, and a high-frequency treatment management part 5000.

In the accompanying drawings, only the main functional parts according to the technical idea may be illustrated, and generally known configurations may be omitted.

The upper end adjustment high-frequency radiating part 1000 is fixed to an upper side portion of a treatment bed 3000 on which a patient 950 is lying. Such an upper side portion may be connected to a corresponding frame of the treatment bed 3000 or may be fixed to a ceiling of a hospital room.

The upper end adjustment high-frequency radiating part 1000 is configured to move an upper end dish-shaped radiating part 4100 in up and down directions and front, rear, left, and right directions and configured to adjust an angle at which a high-frequency signal is radiated, the upper end dish-shaped radiating part 4100 being configured to output a high-frequency signal at a frequency designated by a corresponding control signal applied from the high-frequency treatment management part 5000 to a designated level. Furthermore, the upper end adjustment high-frequency radiating part 1000 is configured to respond with a controlled result. Herein, the designated high-frequency signal designated is a frequency signal in a range of 100 Hz to 15 MHz. Such a high-frequency signal is output wirelessly through an antenna, or is output by direct contact or wired contact as required. Furthermore, the high-frequency signal is radiated into an affected area of the human body.

The upper end adjustment high-frequency radiating part 1000 includes the upper end dish-shaped radiating part 4100, an upper radiating body rotating motor 1010, a first upper moving screw bushing 1020, a first upper screw 1030, a first upper sliding guide 1040, a second upper moving screw bushing 1050, a first upper positioning motor 1060, a second upper screw 1070, a first upper sliding bar 1080, a second upper positioning motor 1090, a second upper sliding guide 1100, a second upper sliding bar 1110, a third upper moving screw bushing 1120, a third upper screw 1130, a third upper positioning motor 1140, and an upper frame part 1150.

The upper end adjustment high-frequency radiating part 1000 is configured to move the upper end dish-shaped radiating part 4100 according to a corresponding control signal of the high-frequency treatment management part 5000 in the up and down directions and the front, rear, left, and right directions within an inner range of a space that the upper frame part 1150 forms. In addition, a position (a focus point) at which a high-frequency signal output from the upper end dish-shaped radiating part 4100 is concentrated is adjusted within a range of a plus minus (+−) 10 degrees by the corresponding control signal of the high-frequency treatment management part 5000. Therefore, even in a specific patient with different physical conditions, a high-frequency signal is accurately radiated into an affected area.

In the description of the lower end adjustment high-frequency radiating part 2000 which has a configuration and an operation similar to those of the upper end adjustment high-frequency radiating part 1000, a duplicate description may be omitted as required, but it should be understood that any explanation provided in one instance applies equally to the other.

The upper end dish-shaped radiating part 4100 outputs a high-frequency signal at a frequency designated by a corresponding control signal of the high-frequency treatment management part 5000, and an angle at which the high-frequency signal is radiated frontward is adjusted. Furthermore, the upper end dish-shaped radiating part 4100 has any one shape selected from a hemispherical parabolic dish shape or a parabolic wing shape formed of at least two parabolic wings.

The upper end dish-shaped radiating part 4100 includes a mounting and fixing origin part 4101, a first base part 4103, a first high-frequency signal element 4105, a first hinge part 4107, a second base part 4109, a second high-frequency signal element 4111, an angle adjustment piston 4113, a second hinge part 4115, and a color light generation part 4117.

Although the first base part 4103, the first high-frequency signal element 4105, the first hinge part 4107, the second base part 4109, the second high-frequency signal element 4111, the angle adjustment piston 4113, the second hinge part 4115, and the color light generation part 4117 are illustrated in the accompanying drawings and are described as having a limited number for explaining the technical idea and the functional configuration, it is evident that the number of each component may be increased or decreased as required.

The mounting and fixing origin part 4101 is formed at a center position of the upper end dish-shaped radiating part 4100, and becomes a rotation center point position on which the upper end dish-shaped radiating part 4100 is fixed and mounted and which is configured to rotate the upper end dish-shaped radiating part 4100 as required.

The mounting and fixing origin part 4101 is formed on the center of the first base part 4103, and the first base part 4103 has a shape of at least two leaves or a generally hemispherical parabolic dish shape. In the drawings, four, three, two leaves shapes and the hemispherical shape are illustrated.

The first high-frequency signal element 4105 is mounted on the first base part 4103, is configured to output a high-frequency signal at a designated frequency and a designated output level by a corresponding control signal of the high-frequency treatment management part 5000, and is provided as at least two first high-frequency signal elements 4105.

That is, when the first base part 4103 is formed in the four leaves shape, the first base part 4105 is formed of four first high-frequency signal elements 4105. When the first base part 4103 is formed in the three leaves shape, the first base part 4105 is formed of three first high-frequency signal elements 4105. When the first base part 4103 is formed in the two leaves shape, the first base part 4105 is formed of two first high-frequency signal elements 4105. In the accompanying drawings, it is illustrated that one first high-frequency signal element 4105 is mounted on each leaf shape, but at least two first high-frequency signal elements 4105 may be mounted on each leaf shape as required. When the first base part 4103 is connected and is formed in the hemispherical shape, the first high-frequency signal element 4105 that is mounted is spaced apart by a uniform distance, and at least two first high-frequency signal elements 4105 are mounted.

The first high-frequency signal element 4105 has the same configuration as a wireless antenna, and is configured such that the first high-frequency signal element 4105 does not directly contact the skin of the human body, but may be configured to be brought into direct contact with the skin of the human body as required.

The first hinge part 4107 is mounted on a border portion of the first base part 4103, and is hinge-coupled to the second base part 4109.

The second base part 4109 is connected to and mounted on an outer portion of the first base part 4103 in a rotatable state by the first hinge part 4107, and is provided as at least two second base parts 4109 or is formed in a hemispherical parabolic dish shape.

The second base part 4109 may be formed in a leaf shape having the same number as the description of the first base part 4103, or may be formed in a generally hemispherical shape.

The second high-frequency signal element 4111 is mounted on the second base part 4109, is configured to output a high-frequency signal at a designated frequency and a designated output level by a corresponding control signal of the high-frequency treatment management part 5000, and is provided as at least two second high-frequency signal elements 4111 as same as the first high-frequency signal element 4105.

A first side end of the angle adjustment piston 4113 is fixed to and mounted on a first side portion of the first base part 4103, and a length of the angle adjustment piston 4113 extends or contracts by a corresponding control signal of the high-frequency treatment management part 5000.

The angle adjustment piston 4113 is mounted such that the first base part 4103 is fixed to and mounted on the first side end of the angle adjustment piston 4113 and the second base part 4109 is hinge-coupled to a second side end of the angle adjustment piston 4113.

The second hinge part 4115 is fixed to a first side end portion of the second base part 4109, and is hinge-coupled to the second side end of the angle adjustment piston 4113.

As the length of the angle adjustment piston 4113 extends or contracts, an angle formed by the first base part 4103 and the second base part 4109 is adjusted, and a focus point on which a high-frequency signal output from the first high-frequency signal element 4105 and the second high-frequency signal element 4111 is concentrated, or a range or a width on which hyperthermia is applied is adjusted.

The color light generation part 4117 is mounted adjacent to the second high-frequency signal element 4111 of the second base part 4109, and a light signal of a red color or a selected color is output by a corresponding control signal of the high-frequency treatment management part 5000. It is very natural that an element in which a selected color among various of colors is output may be used as required. As required, the color light generation part 4117 may be further mounted such that the color light generation part 4117 is mounted adjacent to the first high-frequency signal element 4105.

The high-frequency treatment management part 5000 is configured to control the color light generation part 4117 so that the color light generation part 4117 is operated only when the color light generation part 4117 is required to be operated, and a light signal output from the color light generation part 4117 allows a position where a high-frequency signal is concentrated to be visually identified.

Meanwhile, it is clear that the color light generation part 4117 may not be provided as required.

The upper radiating body rotating motor 1010 is fixed to and mounted on a rear surface position of the upper end dish-shaped radiating part 4100, in which the rear surface position is a position where a high-frequency signal of the upper end dish-shaped radiating part 4100 is not radiated. Furthermore, the upper radiating body rotating motor 1010 is configured to be rotated at a designated speed by a corresponding signal of the high-frequency treatment management part 5000. The high-frequency treatment management part 5000 may adjust a rotation direction, a rotation speed, and a rotation time of the upper radiating body rotating motor 1010. The upper radiating body rotating motor 1010 is formed of a step motor configured to be controlled and rotated by an angle unit of 0.5 degrees so as to be rotated by a specified angle unit. Since the upper radiating body rotating motor 1010 rotates the upper end dish-shaped radiating part 4100, a high-frequency signal that is output and radiated into the human body is effectively radiated to a designated area, thereby increasing the treatment effect.

The first upper moving screw bushing 1020 is fixed to and mounted on the upper radiating body rotating motor 1010, has a tubular shape, and has an inner portion provided with a thread.

The first upper screw 1030 is screw-coupled to the thread inside the first upper moving screw bushing 1020, and is configured to rectilinearly move the first upper moving screw bushing 1020 in a first direction by being rotated.

The first upper sliding guide 1040 is fixed to and mounted on a first side end of the first upper screw 1030 such that the first upper sliding guide 1040 is in a rotatable state, has a tubular shape, and has an inner portion thereof hollow.

The second upper moving screw bushing 1050 is fixed to and mounted on a second side end of the first upper screw 1030 such that the second upper moving screw bushing 1050 is in a rotatable state, has a tubular shape, and has an inner portion provided with a thread.

The first upper positioning motor 1060 is fixed to and mounted on a first side surface of the first upper sliding guide 1040, and is configured to rotate the first upper screw 1030 in a forward direction or a reverse direction by a corresponding control signal of the high-frequency treatment management part 5000. The high-frequency treatment management part 5000 may adjust a rotation time and a rotation speed of the first upper positioning motor 1060.

By driving the first upper moving screw bushing 1020, the first upper screw 1030, and the first upper positioning motor 1060, the upper end dish-shaped radiating part 4100 is moved forward or backward in the first direction, and the first direction is illustrated as an X-axis coordinate direction in the accompanying drawings.

The second upper screw 1070 is fixed to and mounted on the second side end of the first upper screw 1030 such that the second upper screw 1070 is in a rotatable state, is screw-coupled to the thread inside the second upper moving screw bushing 1050, and is configured to rectilinearly move the second upper moving screw bushing 1050 in a second direction by being rotated.

The first upper sliding bar 1080 is inserted into and mounted in the tubular shape of the first upper sliding guide 1040, and is configured to guide the first upper sliding guide 1040 to be moved in a sliding state.

The second upper positioning motor 1090 is connected to and mounted on a second side end of the second upper screw 1070 such that the second upper positioning motor 1090 is in a fixed state, and is configured to rotate the second upper screw 1070 in a forward direction or a reverse direction by a corresponding control signal of the high-frequency treatment management part 5000. The high-frequency treatment management part 5000 may adjust a rotation time and a rotation speed of the second upper positioning motor 1090.

By driving the second upper moving screw bushing 1050, the second upper screw 1070, and the second upper positioning motor 1090, the upper end dish-shaped radiating part 4100 is moved forward or backward in the second direction, and the second direction is illustrated as a Y-axis coordinate direction in the accompanying drawings.

The second upper sliding guide 1100 is fixed to and mounted on a first side end of the second upper screw 1070 such that the second upper sliding guide 1100 is in a rotatable state, has a tubular shape, and has an inner portion thereof hollow.

The second upper sliding bar 1110 is inserted into and mounted in the tubular shape of the second upper sliding guide 1100, and is configured to guide the second upper sliding guide 1100 to be moved in a sliding state.

The third upper moving screw bushing 1120 is fixed to and mounted on a first side end of the first upper sliding bar 1080, has a tubular shape, and has an inner portion provided with a thread.

The third upper screw 1130 is screw-coupled to the thread inside the third upper moving screw bushing 1120, and is configured to rectilinearly move the third upper moving screw bushing 1120 in a third direction by being rotated. Hereinafter, the third direction may be described as a Z-axis direction at the coordinates.

The third upper positioning motor 1140 is connected to and mounted on a first side end of the third upper screw 1130 such that the first upper positioning motor 1140 is in a fixed state, and is configured to rotate the third upper screw 1130 in a forward direction or a reverse direction by a corresponding control signal of the high-frequency treatment management part 5000. The high-frequency treatment management part 5000 may adjust a rotation time and a rotation speed of the third upper positioning motor 1140.

By driving the third upper moving screw bushing 1120, the third upper screw 1130, and the third upper positioning motor 1140, the upper end dish-shaped radiating part 4100 is moved forward or backward in the third direction, and the third direction is illustrated as a Z-axis coordinate direction in the accompanying drawings.

The upper end dish-shaped radiating part 4100 is capable of being moved in the up and down directions and the front, rear, left, and right directions by being moved in the X-axis direction, the Y-axis direction, and the Z-axis direction. Since each of the screws and each of the screw bushings are driven by a ball screw method, fine and precise adjustment of a movement distance is capable of being realized.

The upper frame part 1150 has a hexahedral box shape that forms an external appearance of the upper end adjustment high-frequency radiating part 1000. In the upper frame part 1150, each functional part constituting the upper end adjustment high-frequency radiating part 1000 is mounted in the fixed state or the rotatable state as required.

The upper end dish-shaped radiating part 4100 is configured to be moved in the up and down directions and the front, rear, left, and right directions within an internal space region formed by the upper frame part 1150.

The lower end adjustment high-frequency radiating part 2000 is fixed to and mounted on a lower side portion of the treatment bed 3000 and is embedded inside the treatment bed 3000 on which the patient 950 is lying, the lower side portion of the treatment bed 3000 corresponding to the upper end adjustment high-frequency radiating part 1000. Furthermore, the lower end adjustment high-frequency radiating part 2000 is configured to move a lower end dish-shaped radiating part 4200 in the up and down directions and the front, rear, left, and right directions and is configured to adjust an angle at which a high-frequency signal is radiated, the lower end dish-shaped radiating part 4200 being configured to output a high-frequency signal at a frequency designated by a corresponding control signal to a designated level. Furthermore, the lower end adjustment high-frequency radiating part 2000 is configured to respond with a controlled result.

Since the lower end adjustment high-frequency radiating part 2000 has the same configuration and the same function as the upper end adjustment high-frequency radiating part 1000. Therefore, redundant explanations may be omitted as required, and explanations for such parts can be referred to in the description of the upper end adjustment high-frequency radiating part 1000.

The lower end adjustment high-frequency radiating part 2000 includes the lower end dish-shaped radiating part 4200, a lower radiating body rotating motor 2010, a first lower moving screw bushing 2020, a first lower screw 2030, a first lower sliding guide 2040, a second lower moving screw bushing 2050, a first lower positioning motor 2060, a second lower screw 2070, a first lower sliding bar 2080, a second lower positioning motor 2090, a second lower sliding guide 2100, a second lower sliding bar 2110, a third lower moving screw bushing 2120, a third lower screw 2130, a third lower positioning motor 2140, and a lower frame part 2150.

The lower end dish-shaped radiating part 4200 outputs a high-frequency signal at a frequency designated by a corresponding control signal of the high-frequency treatment management part 5000, and an angle at which the high-frequency signal is radiated frontward is adjusted. Furthermore, the lower end dish-shaped radiating part 4200 has any one shape selected from a hemispherical parabolic dish shape or a parabolic wing shape formed of at least two parabolic wings.

The lower end dish-shaped radiating part 4200 includes a lower end mounting and fixing origin part 4201, a first lower end base part 4203, a first lower end high-frequency signal element 4205, a first lower end hinge part 4207, a second lower end base part 4209, a second lower end high-frequency signal element 4211, a lower end angle adjustment piston 4213, a second lower end hinge part 4215, and a lower end color light generation part 4217.

The lower end mounting and fixing origin part 4201 is formed at the center of the lower end dish-shaped radiating part 4200, and becomes a fixing and mounting position and a rotation center.

The lower end mounting and fixing origin part 4201 is formed on the center of the first lower end base part 4203, and the first lower end base part 4203 is provided as at least two first lower end base parts 4203 or is formed in a hemispherical parabolic dish shape.

The first lower end high-frequency signal element 4205 is mounted on the first lower end base part 4203, is configured to output a high-frequency signal at a designated frequency and a designated output level by a corresponding control signal of the high-frequency treatment management part 5000, and is provided as at least two first lower end high-frequency signal elements 4205.

The first lower end hinge part 4207 is mounted on a border portion of the first lower end base part 4203, and is hinge-coupled to the second lower end base part 4209.

The second lower end base part 4209 is connected to and mounted on an outer portion of the first lower end base part 4203 in a rotatable state by the first lower end hinge part 4207, and is provided as at least two second lower end base parts 4209 or is formed in a hemispherical parabolic dish shape.

The second lower end high-frequency signal element 4211 is mounted on the second lower end base part 4209, is configured to output a high-frequency signal at a designated frequency and a designated output level by a corresponding control signal of the high-frequency treatment management part 5000, and is provided as at least two second lower end high-frequency signal elements 4211.

A first side end of the lower end angle adjustment piston 4213 is fixed to and mounted on a first side portion of the first lower end base part 4203, and a length of the lower end angle adjustment piston 4313 extends or contracts by a corresponding control signal of the high-frequency treatment management part 5000.

The second lower end hinge part 4215 is fixed and mounted on a first side portion of the second lower end base part 4209, and is hinge-coupled to a second side end of the lower end angle adjustment piston 4213.

The lower end color light generation part 4217 is mounted adjacent to the second lower end high-frequency signal element 4211 of the second lower end base part 4209, and a light signal of a red color or a selected color is output by a corresponding control signal of the high-frequency treatment management part 5000. A configuration in which a light signal of a selected color among various colors is output may be used as required. In addition, a configuration in which each light signal of multiple colors selected as required is simultaneously output may be used.

The lower radiating body rotating motor 2010 is fixed to and mounted on a rear surface position of the lower end dish-shaped radiating part 4200, in which the rear surface position is a position where a high-frequency signal of the lower end dish-shaped radiating part 4200 is not radiated. Furthermore, the lower radiating body rotating motor 2010 is configured to be rotated at a designated speed by a corresponding signal of the high-frequency treatment management part 5000. The high-frequency treatment management part 5000 may adjust a rotation direction, a rotation time of the lower radiating body rotating motor 2010.

The first lower moving screw bushing 2020 is fixed to and mounted on the lower radiating body rotating motor 2010, has a tubular shape, and has an inner portion provided with a thread.

The first lower screw 2030 is screw-coupled to the thread inside the first lower moving screw bushing 2020, and is configured to rectilinearly move the first lower moving screw bushing 2020 in a first direction by being rotated.

The first lower sliding guide 2040 is fixed to and mounted on a first side end of the first lower screw 2030 such that the first lower sliding guide 2040 is in a rotatable state, has a tubular shape, and has an inner portion thereof hollow.

The second lower moving screw bushing 2050 is fixed to and mounted on a second side end of the first lower screw 2030 such that the second lower moving screw bushing 2050 is in a rotatable state, has a tubular shape, and has an inner portion provided with a thread.

The first lower positioning motor 2060 is fixed to and mounted on a first side surface of the first lower sliding guide 2040, and is configured to rotate the first lower screw 2030 in a forward direction or a reverse direction by a corresponding control signal of the high-frequency treatment management part 5000. The high-frequency treatment management part 5000 may adjust a rotation speed and a rotation time of the first lower positioning motor 2060.

The second lower screw 2070 is fixed to and mounted on the second side end of the first lower screw 2030, is screw-coupled to the thread inside the second lower moving screw bushing 2050, and is configured to rectilinearly move the second lower moving screw bushing 2050 in a second direction by being rotated.

The first lower sliding bar 2080 is inserted into and mounted in the tubular shape of the first lower sliding guide 2040, and is configured to guide the first lower sliding guide 2040 to be moved in a sliding state.

The second lower positioning motor 2090 is connected to and mounted on a second side end of the second lower screw 2070 such that the second lower positioning motor 2090 is in a fixed state, and is configured to rotate the second lower screw 2070 in a forward direction or a reverse direction by a corresponding control signal of the high-frequency treatment management part 5000. The high-frequency treatment management part 5000 may adjust a rotation speed and a rotation time of the second lower positioning motor 2090.

The second lower sliding guide 2100 is fixed to and mounted on a first side end of the second lower screw 2070 such that the second lower sliding guide 2100 is in a rotatable state, has a tubular shape, and has an inner portion thereof hollow.

The second lower sliding bar 2110 is inserted into and mounted in the tubular shape of the second lower sliding guide 2100, and is configured to guide the second lower sliding guide 2100 to be moved in a sliding state.

The third lower moving screw bushing 2120 is fixed to and mounted on a first side end of the first lower sliding bar 2080, has a tubular shape, and has an inner portion provided with a thread.

The third lower screw 2130 is screw-coupled to the thread inside the third lower moving screw bushing 2120, and is configured to rectilinearly move the third lower moving screw bushing 2120 in a third direction by being rotated.

The third lower positioning motor 2140 is connected to and mounted on a first side end of the third lower screw 2130 such that the first lower positioning motor 2140 is in a fixed state, and is configured to rotate the third lower screw 2130 in a forward direction or a reverse direction by a corresponding control signal of the high-frequency treatment management part 5000. The high-frequency treatment management part 5000 may adjust a rotation speed and a rotation time of the third lower positioning motor 2140.

The lower frame part 2150 has a hexahedral box shape that forms an external appearance of the lower end adjustment high-frequency radiating part 2000.

Although the high-frequency treatment management part 5000 is not specifically illustrated in the drawings, the high-frequency treatment management part 5000 according to the first embodiment is connected to the upper end adjustment high-frequency radiating part 1000 and the lower end adjustment high-frequency radiating part 2000, is configured to control, according to an input command signal, the movement position in the up and down directions and the front, rear, left, and right directions of each of the upper end dish-shaped radiating part 4100 and the lower end dish-shaped radiating part 4200 and an angle at which the high-frequency signal is radiated, is configured to analyze and monitor the received result thereof, is configured to control a frequency and a level of the output high-frequency signal, and is configured to analyze and monitor the received result thereof.

The high-frequency treatment management part 5000 includes a high-frequency hyperthermia treatment management part 5010, a high-frequency signal generation part 5020, a positioning motor operation control part 5030, an affected area size treatment information table 5040, a radiating body angle management part 5050, a treatment information real-time recording part 5060, and an external input/output communication part 5070.

Hereinafter, referring to all the accompanying drawings, an apparatus 900 for treating cancer with high-frequency hyperthermia using an angle-adjustable parabolic-shaped rotating high-frequency radiating body electrode according to a second embodiment of the present disclosure will be described. The apparatus 900 for treating cancer with high-frequency hyperthermia using the angle-adjustable parabolic-shaped rotating high-frequency radiating body electrode according to the second embodiment of the present disclosure includes the upper end adjustment high-frequency radiating part 1000, the lower end adjustment high-frequency radiating part 2000, and a high-frequency treatment management part 5000'.

The second embodiment differs from the first embodiment in the configuration of the upper end dish-shaped radiating part 4100 and the lower end dish-shaped radiating part 4200, as well as in the operation method of the high-frequency treatment management part 5000'. Other components are the same or similar, so identical components will be denoted by the same reference numerals, while different components will be assigned different reference numerals. The entire configuration will be described in detail again.

In the accompanying drawings, only the main functional parts according to the technical idea may be illustrated, and generally known configurations may be omitted.

The upper end adjustment high-frequency radiating part 1000 is fixed to the upper side portion of the treatment bed 3000 on which the patient 950 is lying. Such an upper side portion may be connected to the corresponding frame of the treatment bed 3000 or may be fixed to the ceiling of the hospital room.

The upper end adjustment high-frequency radiating part 1000 is configured to move an upper end dish-shaped radiating part 4100' in the up and down directions and the front, rear, left, and right directions and configured to adjust an angle at which a high-frequency signal is radiated, the upper end dish-shaped radiating part 4100' being configured to output a high-frequency signal at a frequency designated by a corresponding control signal applied from the high-frequency treatment management part 5000' to a designated level. Furthermore, the upper end adjustment high-frequency radiating part 1000 is configured to respond with a controlled result. Herein, the designated high-frequency signal designated is a frequency signal in a range of 100 Hz to 15 MHz. Such a high-frequency signal is output wirelessly through an antenna, or is output by direct contact or wired contact as required. Furthermore, the high-frequency signal is radiated into an affected area of the human body.

The upper end adjustment high-frequency radiating part 1000 includes an upper end dish-shaped radiating part 4100', the first upper moving screw bushing 1020, the first upper screw 1030, the first upper sliding guide 1040, the second upper moving screw bushing 1050, the first upper positioning motor 1060, the second upper screw 1070, the first upper sliding bar 1080, the second upper positioning motor 1090, the second upper sliding guide 1100, the second upper sliding bar 1110, the third upper moving screw bushing 1120, the third upper screw 1130, the third upper positioning motor 1140, and the upper frame part 1150.

The upper end adjustment high-frequency radiating part 1000 is configured to move the upper end dish-shaped radiating part 4100' according to a corresponding control signal of the high-frequency treatment management part 5000' in the up and down directions and the front, rear, left, and right directions within the inner range of a space that the upper frame part 1150 forms. In addition, a position (a focus point) at which a high-frequency signal output from the upper end dish-shaped radiating part 4100' is concentrated is adjusted within a range of a plus minus (+−) 10 degrees by the corresponding control signal of the high-frequency treatment management part 5000'. Therefore, even in a specific patient with different physical conditions, a high-frequency signal is accurately radiated into an affected area.

In the description of the lower end adjustment high-frequency radiating part 2000 which has a configuration and an operation similar to those of the upper end adjustment high-frequency radiating part 1000, a duplicate description may be omitted as required, but it should be understood that any explanation provided in one instance applies equally to the other.

The upper end dish-shaped radiating part 4100' outputs a high-frequency signal at a frequency designated by a corresponding control signal of the high-frequency treatment management part 5000', and has any one shape selected from a hemispherical parabolic dish shape or a parabolic wing shape formed of at least two parabolic wings.

The upper end dish-shaped radiating part 4100' includes the mounting and fixing origin part 4101, the first base part 4103, and the first high-frequency signal element 4105.

Although the first base part 4103 and the first high-frequency signal element 4105 illustrated in the accompanying drawings are illustrated and explained as having limited numbers for explaining technical ideas and functional configurations, it is very natural that the first base part 4103 and the first high-frequency signal element 4105 can be increased or decreased as necessary.

The mounting and fixing origin part 4101 is formed at the center position of the upper end dish-shaped radiating part 4100', and becomes a rotation center point position on which the upper end dish-shaped radiating part 4100' is fixed and mounted and which is configured to rotate the upper end dish-shaped radiating part 4100' as required.

The mounting and fixing origin part 4101 is formed on the center of the first base part 4103, and the first base part 4103 has a shape of at least two leaves or a generally hemispherical parabolic dish shape. In the drawings, four, three, two leaves shapes and the hemispherical shape are illustrated.

The first high-frequency signal element 4105 is mounted on the first base part 4103, and is configured to output a high-frequency signal at a designated frequency and a designated output level by a corresponding control signal of the high-frequency treatment management part 5000'. Furthermore, although it is illustrated in the drawings that one first high-frequency signal element 4105 is provided, the first high-frequency signal element 4105 may be provided as at least two first high-frequency signal elements 4105.

That is, when the first base part 4103 is formed in the four leaves shape, the first base part 4105 is formed of four first high-frequency signal elements 4105. When the first base part 4103 is formed in the three leaves shape, the first base part 4105 is formed of three first high-frequency signal elements 4105. When the first base part 4103 is formed in the two leaves shape, the first base part 4105 is formed of two first high-frequency signal elements 4105. In the accompanying drawings, it is illustrated that one first high-frequency signal element 4105 is mounted on each leaf shape, but at least two first high-frequency signal elements 4105 may be mounted on each leaf shape as required. When the first base part 4103 is connected and is formed in the hemispherical shape, the first high-frequency signal element 4105 that is mounted is spaced apart by a uniform distance, and at least two first high-frequency signal elements 4105 are mounted.

In the accompanying drawings, since an embodiment in which the first base part 4103 is divided into six regions is illustrated, each first high-frequency signal element 4105 is respectively mounted on each of divided regions, so that six first high-frequency signal elements 4105 are mounted. However, each region may be increased or decreased as required. Accordingly, the number of mounted first high-frequency signal elements 4105 is also increased or decreased at the same time.

The first high-frequency signal element 4105 has the same configuration as a wireless antenna, and is configured such that the first high-frequency signal element 4105 does not directly contact the skin of the human body, but may be configured to be brought into direct contact with the skin of the human body as required.

The high-frequency treatment management part 5000' may control the first high-frequency signal element 4105 such that the plurality of first high-frequency signal elements 4105 is operated simultaneously in a situation in which at least two first high-frequency signal elements 4105 are mounted. Otherwise, as illustrated in FIG. 10, the high-frequency treatment management part 5000' may control the first high-frequency signal element 4105 such that each first high-frequency signal element 4105 provided in the order of A, B, C, D, E, and F is respectively operated for a specific period of time.

In FIG. 10, it is illustrated that six first high-frequency signal elements 4105 provided in A, B, C, D, E, and F are described as an example. Meanwhile, as illustrated in FIG. 11, two, three, four, five, or seven or more first high-frequency signal elements 4105 may be configured (provided) as required.

The operation time of each of the first high-frequency signal elements 4105 may be adjusted and selected for treatment purposes. For example, the operation time may be selected or simultaneously selected in overlapping units of 1 second, 5 seconds, 10 seconds, 20 seconds, 30 seconds, 1 minute, 5 minutes, and 10 minutes, so that the required treatment time may be adjusted.

It is preferable that the high-frequency treatment management unit 5000' is configured to control the upper end dish-shaped radiating part 4100' and a lower end dish-shaped radiating part 4200' to be operated in the same manner. Furthermore, the high-frequency treatment management unit 5000' may operate all of the first high-frequency signal elements 4105 to be operated in an activated state, or may operate each first high-frequency signal element 4105 to be operated in a reverse order, an irregular order, a selective order, or a random order. That is, each first high-frequency signal element 4105 is capable of being operated selectively for the desired treatment effect and the purpose.

The first upper moving screw bushing 1020 has the tubular shape, and has the inner portion provided with the thread.

The first upper screw 1030 is screw-coupled to the thread inside the first upper moving screw bushing 1020, and is configured to rectilinearly move the first upper moving screw bushing 1020 in the first direction by being rotated.

The first upper sliding guide 1040 is fixed to and mounted on the first side end of the first upper screw 1030 such that the first upper sliding guide 1040 is in the rotatable state, has the tubular shape, and has the inner portion thereof hollow.

The second upper moving screw bushing 1050 is fixed to and mounted on the second side end of the first upper screw 1030 such that the second upper moving screw bushing 1050 is in a rotatable state, has a tubular shape, and has the inner portion provided with the thread.

The first upper positioning motor 1060 is fixed to and mounted on the first side surface of the first upper sliding guide 1040, and is configured to rotate the first upper screw 1030 in the forward direction or the reverse direction by a corresponding control signal of the high-frequency treatment management part 5000'. The high-frequency treatment management part 5000' may adjust the rotation time and the rotation speed of the first upper positioning motor 1060.

By driving the first upper moving screw bushing 1020, the first upper screw 1030, and the first upper positioning motor 1060, the upper end dish-shaped radiating part 4100' is moved forward or backward in the first direction, and the first direction is illustrated as the X-axis coordinate direction in the accompanying drawings.

The second upper screw 1070 is fixed to and mounted on the second side end of the first upper screw 1030 such that the second upper screw 1070 is in the rotatable state, is screw-coupled to the thread inside the second upper moving screw bushing 1050, and is configured to rectilinearly move the second upper moving screw bushing 1050 in the second direction by being rotated.

The first upper sliding bar 1080 is inserted into and mounted in the tubular shape of the first upper sliding guide 1040, and is configured to guide the first upper sliding guide 1040 to be moved in the sliding state.

The second upper positioning motor 1090 is connected to and mounted on the second side end of the second upper screw 1070 such that the second upper positioning motor 1090 is in the fixed state, and is configured to rotate the second upper screw 1070 in the forward direction or the reverse direction by the corresponding control signal of the high-frequency treatment management part 5000'. The high-frequency treatment management part 5000' may adjust the rotation time and the rotation speed of the second upper positioning motor 1090.

By driving the second upper moving screw bushing 1050, the second upper screw 1070, and the second upper positioning motor 1090, the upper end dish-shaped radiating part 4100' is moved forward or backward in the second direction, and the second direction is illustrated as the Y-axis coordinate direction in the accompanying drawings.

The second upper sliding guide 1100 is fixed to and mounted on the first side end of the second upper screw 1070 such that the second upper sliding guide 1100 is in the rotatable state, has the tubular shape, and has the inner portion thereof hollow.

The second upper sliding bar 1110 is inserted into and mounted in the tubular shape of the second upper sliding guide 1100, and is configured to guide the second upper sliding guide 1100 to be moved in the sliding state.

The third upper moving screw bushing 1120 is fixed to and mounted on the first side end of the first upper sliding bar 1080, has the tubular shape, and has the inner portion provided with the thread.

The third upper screw 1130 is screw-coupled to the thread inside the third upper moving screw bushing 1120, and is configured to rectilinearly move the third upper moving screw bushing 1120 in the third direction by being rotated. Hereinafter, the third direction may be described as the Z-axis direction at the coordinates.

The third upper positioning motor 1140 is connected to and mounted on the first side end of the third upper screw 1130 such that the first upper positioning motor 1140 is in the fixed state, and is configured to rotate the third upper screw 1130 in the forward direction or the reverse direction by the corresponding control signal of the high-frequency treatment management part 5000'. The high-frequency treatment management part 5000' may adjust the rotation time and the rotation speed of the third upper positioning motor 1140.

By driving the third upper moving screw bushing 1120, the third upper screw 1130, and the third upper positioning motor 1140, the upper end dish-shaped radiating part 4100' is moved forward or backward in the third direction, and the third direction is illustrated as the Z-axis coordinate direction in the accompanying drawings.

The upper end dish-shaped radiating part 4100' is capable of being moved in the up and down directions and the front, rear, left, and right directions by being moved in the X-axis direction, the Y-axis direction, and the Z-axis direction. Since each of the screws and each of the screw bushings are driven by the ball screw method, the fine and precise adjustment of the movement distance is capable of being realized.

The upper frame part 1150 has the hexahedral box shape that forms the external appearance of the upper end adjustment high-frequency radiating part 1000. In the upper frame part 1150, each functional part constituting the upper end adjustment high-frequency radiating part 1000 is mounted in the fixed state or the rotatable state as required.

The upper end dish-shaped radiating part 4100' is configured to be moved in the up and down directions and the front, rear, left, and right directions within an internal space region formed by the upper frame part 1150.

The lower end adjustment high-frequency radiating part 2000 is fixed to and mounted on the lower side portion of the treatment bed 3000 and is embedded inside the treatment bed 3000 on which the patient 950 is lying, the lower side portion of the treatment bed 3000 corresponding to the upper end adjustment high-frequency radiating part 1000. Furthermore, the lower end adjustment high-frequency radiating part 2000 is configured to move the lower end dish-shaped radiating part 4200' in the up and down directions and the front, rear, left, and right directions and is configured to adjust an angle at which a high-frequency signal is radiated, the lower end dish-shaped radiating part 4200' being configured to output a high-frequency signal at a frequency designated by a corresponding control signal to a designated level. Furthermore, the lower end adjustment high-frequency radiating part 2000 is configured to respond with a controlled result.

Since the lower end adjustment high-frequency radiating part 2000 has the same configuration and the same function as the upper end adjustment high-frequency radiating part 1000. Therefore, redundant explanations may be omitted as required, and explanations for such parts can be referred to in the description of the upper end adjustment high-frequency radiating part 1000.

The lower end adjustment high-frequency radiating part 2000 includes the lower end dish-shaped radiating part 4200', the first lower moving screw bushing 2020, the first lower screw 2030, the first lower sliding guide 2040, the second lower moving screw bushing 2050, the first lower positioning motor 2060, the second lower screw 2070, the first lower sliding bar 2080, the second lower positioning motor 2090, the second lower sliding guide 2100, the second lower sliding bar 2110, the third lower moving screw bushing 2120, the third lower screw 2130, the third lower positioning motor 2140, and the lower frame part 2150.

The lower end dish-shaped radiating part 4200' outputs a high-frequency signal at a frequency designated by a corresponding control signal of the high-frequency treatment management part 5000', and an angle at which the high-frequency signal is radiated frontward is adjusted. Furthermore, the lower end dish-shaped radiating part 4200' has any one shape selected from the hemispherical parabolic dish shape or the parabolic wing shape formed of at least two parabolic wings.

The lower end dish-shaped radiating part 4200' includes the lower end mounting and fixing origin part 4201, the first lower end base part 4203, and the first lower end high-frequency signal element 4205.

The lower end mounting and fixing origin part 4201 is formed at the center of the lower end dish-shaped radiating part 4200', and becomes the fixing and mounting position and the rotation center.

The lower end mounting and fixing origin part 4201 is formed on the center of the first lower end base part 4203, and the first lower end base part 4203 is provided as at least two first lower end base parts 4203 or is formed in a hemispherical parabolic dish shape.

The first lower end high-frequency signal element 4205 is mounted on the first lower end base part 4203, is configured to output a high-frequency signal at a designated frequency and a designated output level by a corresponding control signal of the high-frequency treatment management part 5000', and is provided as at least two first lower end high-frequency signal elements 4205.

The first lower moving screw bushing 2020 has the tubular shape, and has the inner portion provided with the thread.

The first lower screw 2030 is screw-coupled to the thread inside the first lower moving screw bushing 2020, and is configured to rectilinearly move the first lower moving screw bushing 2020 in the first direction by being rotated.

The first lower sliding guide 2040 is fixed to and mounted on the first side end of the first lower screw 2030 such that the first lower sliding guide 2040 is in the rotatable state, has the tubular shape, and has the inner portion thereof hollow.

The second lower moving screw bushing 2050 is fixed to and mounted on the second side end of the first lower screw 2030 such that the second lower moving screw bushing 2050 is in the rotatable state, has the tubular shape, and has the inner portion provided with the thread.

The first lower positioning motor 2060 is fixed to and mounted on the first side surface of the first lower sliding guide 2040, and is configured to rotate the first lower screw 2030 in the forward direction or the reverse direction by a corresponding control signal of the high-frequency treatment management part 5000'. The high-frequency treatment management part 5000' may adjust the rotation speed and the rotation time of the first lower positioning motor 2060.

The second lower screw 2070 is fixed to and mounted on the second side end of the first lower screw 2030, is screw-coupled to the thread inside the second lower moving screw bushing 2050, and is configured to rectilinearly move the second lower moving screw bushing 2050 in the second direction by being rotated.

The first lower sliding bar 2080 is inserted into and mounted in the tubular shape of the first lower sliding guide 2040, and is configured to guide the first lower sliding guide 2040 to be moved in the sliding state.

The second lower positioning motor 2090 is connected to and mounted on the second side end of the second lower screw 2070 such that the second lower positioning motor 2090 is in the fixed state, and is configured to rotate the second lower screw 2070 in the forward direction or the reverse direction by a corresponding control signal of the high-frequency treatment management part 5000'. The high-frequency treatment management part 5000' may adjust the rotation speed and the rotation time of the second lower positioning motor 2090.

The second lower sliding guide 2100 is fixed to and mounted on the first side end of the second lower screw 2070 such that the second lower sliding guide 2100 is in the rotatable state, has the tubular shape, and has the inner portion thereof hollow.

The second lower sliding bar 2110 is inserted into and mounted in the tubular shape of the second lower sliding guide 2100, and is configured to guide the second lower sliding guide 2100 to be moved in the sliding state.

The third lower moving screw bushing 2120 is fixed to and mounted on the first side end of the first lower sliding bar 2080, has the tubular shape, and has the inner portion provided with the thread.

The third lower screw 2130 is screw-coupled to the thread inside the third lower moving screw bushing 2120, and is configured to rectilinearly move the third lower moving screw bushing 2120 in the third direction by being rotated.

The third lower positioning motor 2140 is connected to and mounted on the first side end of the third lower screw 2130 such that the first lower positioning motor 2140 is in the fixed state, and is configured to rotate the third lower screw 2130 in the forward direction or the reverse direction by a corresponding control signal of the high-frequency treatment management part 5000'. The high-frequency treatment management part 5000' may adjust the rotation speed and the rotation time of the third lower positioning motor 2140.

The lower frame part 2150 has the hexahedral box shape that forms the external appearance of the lower end adjustment high-frequency radiating part 2000.

The high-frequency treatment management part 5000' is connected to the upper end adjustment high-frequency radiating part 1000 and the lower end adjustment high-frequency radiating part 2000, is configured to control, according to an input command signal, the movement position in the up and down directions and the front, rear, left, and right directions of each of the upper end dish-shaped radiating part 4100' and the lower end dish-shaped radiating part 4200' and an angle at which the high-frequency signal is radiated, is configured to analyze and monitor the received result thereof, is configured to control a frequency and a level of the output high-frequency signal, and is configured to analyze and monitor the received result thereof.

The high-frequency treatment management part 5000' includes the high-frequency hyperthermia treatment management part 5010, the high-frequency signal generation part 5020, the positioning motor operation control part 5030, the affected area size treatment information table 5040, the radiating body angle management part 5050, the treatment information real-time recording part 5060, and the external input/output communication part 5070.

When an energy of the high-frequency (or radio frequency) signal generated between electrodes is transmitted (injected, infused, inputted, radiated) to the body tissue, the biological tissue positioned between the electrodes generates bioheat by an average of 3 degrees Celsius to 5 degrees Celsius. When the energy is focused on a specific area, the body temperature at the corresponding region may increase by approximately 7 degrees Celsius.

Such a high-frequency hyperthermia method realizes heat generated in the cell to be transferred to the outside from the inside. Particularly, such a high-frequency hyperthermia method may be intensively applied on the damaged tissue, so that highly efficient treatment may be realized.

Meanwhile, it is known that the biological cell is destroyed when the temperature thereof increases to 47 degrees Celsius, and the cancer cell is destroyed in a range of approximately 42 degrees Celsius. Therefore, when the hyperthermia is applied such that a region around the cancer cell is heated to a temperature of 42 degrees Celsius, a situation in which only the cancer cell dies occurs. Therefore, one of the technical idea of the present disclosure is to realize such a situation locally and only at the location where the cancer cell is positioned.

A treatment mode using the high-frequency hyperthermia method is divided into two types that are a CET mode and a RET mode. The CET mode activates regenerative circulation of the skin tissue near the skin surface, acts on the specific fat cell to promote venous blood circulation, enhances skin tissue regeneration, and facilitates the breakdown and elimination of the fat cell.

The RET mode delivers high-frequency energy at a safe and specific frequency to a depth of several centimeters (Cm) within the skin tissue, quickly alleviates stiff nodular masses, regenerates elastin and collagen fibers, dissolves fat without damaging the biological tissue, and realizes an effective body lifting, thereby managing an obese body type. That is, the RET mode burns the body fat, discharges the cellulite, relieves the pain caused by circulation disorders, removes the aging cell, releases the muscle that is bound or rigid, and discharges toxins.

Elastin is a protein having a high elastic force in the connective tissue, and is capable of maintaining a shape after numerous internal tissues are expanded or contracted. Elastin helps the skin return to the original position thereof when the skin is pressed or tightened. Elastin is an important supporting capacity tissue in the body of a vertebrate animal, and dynamic energy is required for storage. In humans, elastin is encoded by the ELN gene.

Elastin in the body is connected to other proteins of the connective tissue, and forms a composite of amorphous elastin and fibrillin fibers. These two components mainly consist of smaller amino acids such as glycine, valine, alanine, and proline.

By increasing the body temperature of the internal tissues of the body, the body enhances resistance and immunity, activates cellular functions to regulate biological balance, and improves blood circulation through elevated body temperature and vasodilation, so that swelling and inflammation are reduced. Furthermore, the absorption of oxygen and nutrients is increased, the secretion of fluids such as lymph fluid is increased, the production of active oxygen species is suppressed, and the metabolism is promoted by promoting the cell activation.

Cancer is not one single disease but rather a group of diseases with common characteristics that often result in sustained cell proliferation, reduced or delayed cell mortality, cooption of bodily angiogenesis and metabolic processes and evasion of bodily immune response which results in undesirable soft tissue growths called neoplasms or, more commonly, tumors.

Removal or destruction of this aberrant tissue is a goal of many cancer treatment methods and modalities. Surgical tumor excision is one method of accomplishing this goal.

Tissue ablation is another minimally invasive method of destroying undesirable tissue in the body, and has been generally divided into thermal and non-thermal ablation techniques. Thermal ablation encompasses both the addition and removal of heat to destroy undesirable cells. Cryoablation is a technique that kills cells by freezing of the extracellular compartment resulting in cell dehydration beginning at −15 degrees Celsius and by intracellular ice formation causing membrane rupture occurring at colder temperatures. Because cryoablative techniques can rupture the cell membrane without denaturing cell proteins under certain conditions, such techniques have the additional ability to stimulate an antitumor immune response in the patient.

In the present disclosure having the configuration described above, since a cross-sectional area of the high-frequency radiating body electrode radiating a high-frequency signal to an affected area of a patient is formed in a curved shaped of a parabola, the generated high-frequency signal is concentrated on a specific position, so that there is an effect that the treatment effect is increased. Furthermore, since the high-frequency radiating body electrode configured to radiate the high-frequency signal to the affected area of the patient is formed in any one shape selected from the parabolic wing shape or the parabolic hemispherical shape, the extent to which the high-frequency signal is concentrated is adjusted, so that there is an effect that the treatment effect is increased. Furthermore, since the position of the high-frequency radiating body electrode configured to radiate the high-frequency signal to the affected area of the patient is moved in the up and down directions and the front, rear, left, and right directions, there is an effect that the radiation of the high-frequency signal to the designated affected area is easily performed in a state in which the patient is not moving. Furthermore, since the frequency and the output level of the high-frequency signal output from the high-frequency radiating body configured to radiate the high-frequency signal to the affected area of the patient are adjusted according to the size of the affected area and the depth which is measured from the skin or which is expected, there is an effect that the treatment effect is increased.

The present disclosure has been described in detail with respect to the described embodiments. However, it is obvious to those skilled in the art that various modifications and changes may be derived within the scope of the technical spirit of the present disclosure, and it is natural that such modifications and changes belong to the appended claims.

The invention claimed is:

1. An apparatus for treating cancer with high-frequency hyperthermia using an angle-adjustable parabolic-shaped rotating high-frequency radiating body electrode, the apparatus comprising:

an upper end adjustment high-frequency radiating part (1000) fixed to and mounted on an upper side portion of a treatment bed (3000) on which a patient (950) is lying, the upper end adjustment high-frequency radiating part (1000) being configured to move an upper end dish-shaped radiating part (4100') in up and down directions and front, rear, left, and right directions and being configured to adjust an angle at which a high-frequency signal is radiated and being configured to respond with a controlled result, the upper end dish-shaped radiating part (4100') being configured to output a high-frequency signal at a frequency designated by a corresponding control signal to a designated level; and a lower end adjustment high-frequency radiating part (2000) fixed to and mounted on a lower side portion of the treatment bed (3000) corresponding to the upper end adjustment high-frequency radiating part (1000) and embedded inside the treatment bed (3000) on which the patient (950) is lying, the lower end adjustment high-frequency radiating part (2000) being configured to move a lower end dish-shaped radiating part (4200') in the up and down directions and the front, rear, left, and right directions and being configured to adjust an angle at which a high-frequency signal is radiated and being configured to respond with a controlled result, the lower end dish-shaped radiating part (4200') being configured to output a high-frequency signal at a frequency designated by a corresponding control signal to a designated level, wherein the upper end adjustment high-frequency radiating part (1000) comprises:

the upper end dish-shaped radiating part (4100') configured to output a high-frequency signal at a frequency designated by a corresponding control signal and configured to radiate the high-frequency signal frontward, the upper end dish-shaped radiating part (4100') having any one shape selected from a hemispherical parabolic dish shape or a parabolic wing shape formed of at least two parabolic wings;

a first upper moving screw bushing (1020) fixed to and mounted on the upper end dish-shaped radiating part (4100'), the first upper moving screw bushing (1020) having a tubular shape in which a center in a longitudinal direction thereof is penetrated, and the first upper moving screw bushing (1020) having an inner portion thereof provided with a thread;

a first upper screw (1030) screw-coupled to the thread inside the first upper moving screw bushing (1020), the first upper screw (1030) being configured to rectilinearly move the first upper moving screw bushing (1020) in a first direction by being rotated;

a first upper sliding guide (1040) fixed to and mounted on a first side end of the first upper screw (1030) such that the first upper sliding guide (1040) is in a rotatable state, the first upper sliding guide (1040) having a tubular shape and having an inner portion thereof hollow;

a second upper moving screw bushing (1050) fixed to and mounted on a second side end of the first upper screw (1030) such that the second upper moving screw bushing (1050) is in a rotatable state, the second upper moving screw bushing (1050) having a tubular shape and having an inner portion thereof provided with a thread;

a first upper positioning motor (1060) fixed to and mounted on a first side surface of the first upper sliding guide (1040), the first upper positioning motor (1060) being configured to rotate the first upper screw (1030) in a forward direction or a reverse direction by a corresponding control signal; and a second upper screw (1070) fixed to and mounted on the second side end of the first upper screw (1030) such that the second upper screw (1070) is in a rotatable state, the second upper screw (1070) being screw-coupled to the thread inside the second upper moving screw bushing (1050), and the second upper screw (1070) being configured to rectilinearly move the second upper moving screw bushing (1050) in a second direction by being rotated.

2. The apparatus of claim 1, wherein the upper end adjustment high-frequency radiating part (1000) further comprises:

a first upper sliding bar (1080) inserted into and mounted in the tubular shape of the first upper sliding guide (1040), the first upper sliding bar (1080) being configured to guide the first upper sliding guide (1040) to be moved in a sliding state;

a second upper positioning motor (1090) connected to and mounted on a second side end of the second upper screw (1070) such that the second upper positioning motor (1090) is in a fixed state, the second upper positioning motor (1090) being configured to rotate the second upper screw (1070) in a forward direction or a reverse direction by a corresponding control signal;

a second upper sliding guide (1100) fixed to and mounted on a first side end of the second upper screw (1070) such that the second upper sliding guide (1100) is in a rotatable state, the second upper sliding guide (1100) having a tubular shape and having an inner portion thereof hollow;

a second upper sliding bar (1110) inserted into and mounted in the tubular shape of the second upper sliding guide (1100), the second upper sliding bar (1110) being configured to guide the second upper sliding guide (1100) to be moved in a sliding state;

a third upper moving screw bushing (1120) fixed to and mounted on a first side end of the first upper sliding bar (1080), the third upper moving screw bushing (1120) having a tubular shape and having an inner portion thereof provided with a thread;

a third upper screw (1130) screw-coupled to the thread inside the third upper moving screw bushing (1120), the third upper screw (1130) being configured to rectilinearly move the third upper moving screw bushing (1120) in a third direction by being rotated;

a third upper positioning motor (1140) connected to and mounted on a first side end of the third upper screw (1130), the third upper positioning motor (1140) being configured to rotate the third upper screw (1130) in a forward direction or a reverse direction by a corresponding control signal; and an upper frame part (1150) having a hexahedral box shape that forms an external appearance of the upper end adjustment high-frequency radiating part (1000).

3. The apparatus of claim 1, wherein the upper end dish-shaped radiating part (4100') comprises:

a mounting and fixing origin part (4101) which is formed at a center of the upper end dish-shaped radiating part (4100') and which is a center of a fixing and mounting position;

a first base part (4103) having a center provided with the mounting and fixing origin part (4101), the first base part (4103) being provided as at least two first base parts (4103) or being formed in a hemispherical parabolic dish shape; and a first high-frequency signal element (4105) mounted on the first base part (4103), the first high-frequency signal element (4105) being configured to output a high-frequency signal at a designated frequency and a designated output level by a corresponding control signal of a high-frequency treatment management part (5000'), and the first high-frequency signal element (4105) being provided as at least two first high-frequency signal elements (4105).

* * * * *